United States Patent
Chapman

(10) Patent No.: US 11,745,182 B2
(45) Date of Patent: Sep. 5, 2023

(54) COLLAPSIBLE CENTRIFUGATION VIAL SYSTEM AND METHOD

(71) Applicant: Stem Cell Partners, LLC, Sacramento, CA (US)

(72) Inventor: John R. Chapman, Sacramento, CA (US)

(73) Assignee: Stem Cell Partners, LLC, Sacramento, CA (US)

( * ) Notice: Subject to any disclaimer, the term of this patent is extended or adjusted under 35 U.S.C. 154(b) by 683 days.

(21) Appl. No.: 16/738,277

(22) Filed: Jan. 9, 2020

(65) Prior Publication Data
US 2020/0215533 A1 Jul. 9, 2020

Related U.S. Application Data

(60) Provisional application No. 62/790,124, filed on Jan. 9, 2019.

(51) Int. Cl.
| | | |
|---|---|---|
| *B01L 3/00* | (2006.01) | |
| *B01L 9/00* | (2006.01) | |
| *B04B 5/04* | (2006.01) | |
| *B01D 15/10* | (2006.01) | |

(52) U.S. Cl.
CPC .............. *B01L 3/505* (2013.01); *B01D 15/10* (2013.01); *B01L 9/00* (2013.01); *B04B 5/0428* (2013.01); *B01L 2300/0681* (2013.01); *B01L 2300/0832* (2013.01); *B01L 2300/0858* (2013.01); *B01L 2300/12* (2013.01); *B01L 2400/06* (2013.01)

(58) Field of Classification Search
CPC .... B01L 3/505; B01L 9/00; B01L 2300/0681; B01L 2300/0832; B01L 2300/12; B01L 2300/0858; B01L 2400/06; B01D 15/10; B04B 5/0428
See application file for complete search history.

(56) References Cited

U.S. PATENT DOCUMENTS

| | | |
|---|---|---|
| 5,766,149 A | 6/1998 | Kriesel et al. |
| 5,859,374 A | 1/1999 | Mink et al. |
| 2002/0064484 A1* | 5/2002 | Lin ...................... B01L 3/50825 422/561 |
| 2006/0175242 A1 | 8/2006 | Dorian et al. |
| 2008/0017530 A1 | 1/2008 | Bras et al. |

(Continued)

*Primary Examiner* — Brian R Gordon
*Assistant Examiner* — Dwan A Gerido
(74) *Attorney, Agent, or Firm* — Heisler & Associates

(57) ABSTRACT

A vial and system are configured to simplify fluid input and extraction therefrom. The vial has a first end opposite a second end and with a collapsible sidewall. The sidewall can be collapsed, such as by imparting a differential pressure between an interior and exterior of the vial, for simplified fluid extraction and smooth extraction without disturbing boundaries between separated components. The vial typically has a bulb at a first end and a neck extending away from the bulb and toward the second end. An inlet spaced from the first end can be configured to attach to various different interfaces or processing elements for input and output of fluids. A support cup can be provided for use with the vial during centrifugation to allow the vial to withstand any centrifugation forces. Various fluid processing methodologies are supported by the collapsible vial, especially including methods of separation of components of blood.

10 Claims, 7 Drawing Sheets

(56) References Cited

U.S. PATENT DOCUMENTS

2013/0045852 A1* 2/2013 Chapman .............. B01D 21/26
 494/36
2015/0343458 A1 12/2015 Chapman et al.

* cited by examiner

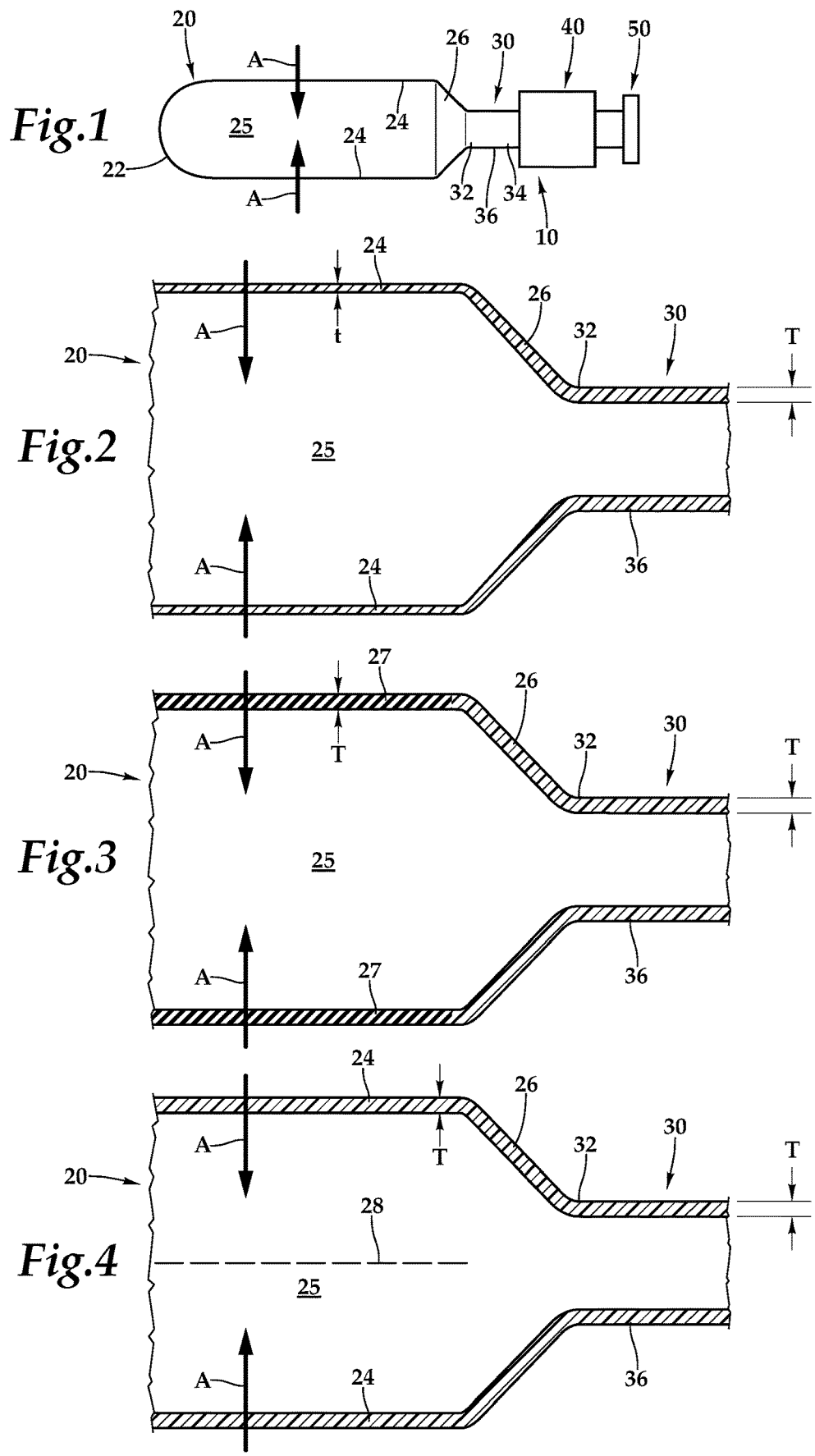

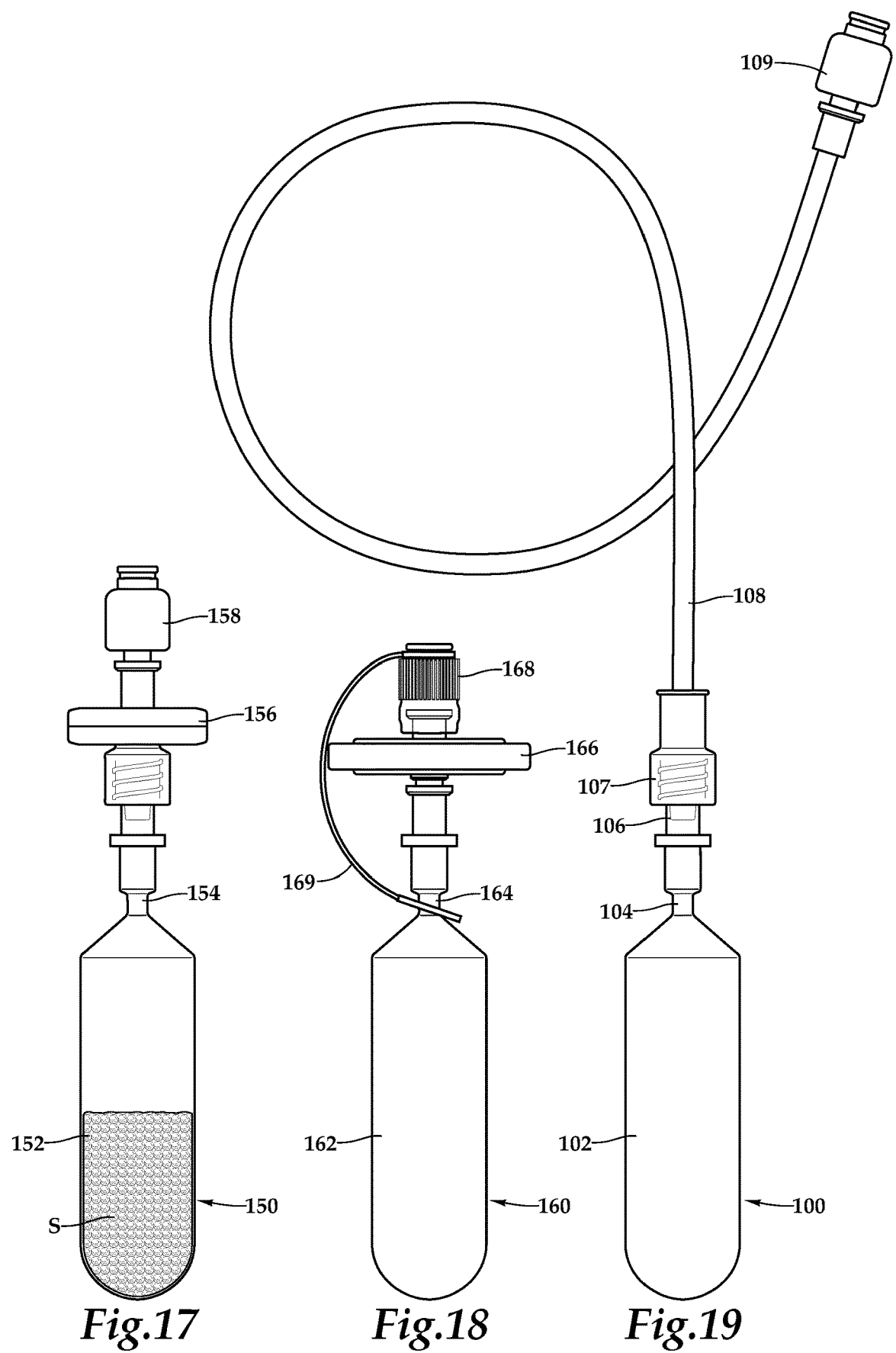
*Fig.17*  *Fig.18*  *Fig.19*

COLLAPSIBLE CENTRIFUGATION VIAL SYSTEM AND METHOD

CROSS-REFERENCE TO RELATED APPLICATIONS

This application claims benefit under Title 35, United States Code § 119(e) of U.S. Provisional Application No. 62/790,124 filed on Jan. 9, 2019.

FIELD OF THE INVENTION

The field of this invention relates generally to separation of mixtures by centrifugation and the vessels, assemblies and methods employed during centrifugation to achieve extraction and purification of target particles from non-target particles of the mixture based upon differences in particle size and density. More particularly, this invention relates to methods of separation of components of a fluid mixture, such as blood, with centrifugation vials having a collapsible sidewall.

BACKGROUND OF THE INVENTION

The background of centrifugation and centrifugation devices was reviewed in U.S. Pat. No. 9,101,925, the entire contents of which are incorporated herein by reference.

The technique of separating peripheral blood mononuclear cells (PBMCs) from whole blood was developed approximately 50 years ago (Bøyum, A., *Scand. J. Clin. Lab. Invest.* 21 Suppl. 97, 31 (1968) and Bøyum, A., *Scand. J. Clin. Lab. Invest.* 21 Suppl. 97, 77 (1968)). This technique has been used worldwide to collect and study lymphocytes and monocytes from a variety of subjects and in a variety of diseases (Kaplan, J., et al., *J. Immunol. Methods* 50:187 (1982), Hirvonen, H., et al., *Blood* 78:3012 (1991), Suhadolnik, R., et al., J. Interferon & Cytokine Res. 17:377 (1997).

The current method of isolation of PBMCs requires separation of whole blood by centrifugation through a density gradient is summarized below.

Whole blood is layered onto a sterile aqueous medium containing ficoll and sodium diatrizoate at a predetermined density of 1.077 g/ml at 25° C. Gentle centrifugation at room temperature results in the separation of PBMCs at the blood/ficoll interface, with the other white blood cells (WBCs) and red blood cells (RBCs) passing through the interface and collecting at the bottom of the tube. The PBMC interface is the collected and washed with sterile Phosphate Buffered Saline (PBS) to remove any contaminating separation medium. The PBMCs are then subjected to a brief treatment with a hypotonic aqueous medium containing ammonium chloride to lyse any contaminating RBCs present.

Ficoll-Paque™ (GE Healthcare, Uppsala, Sweden) are commercial products that are sterile, ready-to-use density gradient media for isolating mononuclear cells in high yield and purity from small or large volumes of human peripheral blood, using a simple and rapid centrifugation procedure based on the method developed by Bøyum. Ficoll-Paque products can also be used to prepare purified mononuclear cells from sources other than human peripheral blood including bone marrow, adipose and umbilical cord blood. Separation of normal whole human peripheral blood by the procedure typically yields a mononuclear cell preparation with:

60±20% recovery of the mononuclear cells present in the original blood sample
95±5% mononuclear cells
>80% viability of the separated cells
Maximum 5% granulocytes
Maximum 10% erythrocytes Source: General Electric Company, GE Healthcare Bio-Sciences AB, pamphlet entitled "Isolation of Mononuclear Cells, Methodology and Applications," first published June 1983 and updated as recently as 2014, accessed on Dec. 18, 2019 at https://us.vwr.com/assetsvc/asset/en_US/id/16286835/contents.

Ficoll-Paque density gradient media products are aqueous solutions containing Ficoll PM400 and sodium diatrizoate with calcium di sodium ethylenediamine-tetraacetic acid. Ficoll PM400 is a synthetic high molecular weight (Mr 400 000) polymer of sucrose and epichlorohydrin which is readily soluble in water. Sodium diatrizoate is a convenient compound to use with Ficoll PM400 since it forms solutions of low viscosity with high density. The function of sodium diatrizoate in Ficoll-Paque products is to provide the optimal density and osmolarity necessary for the efficient removal of other cells from the mononuclear cells. Ficoll-Paque products are typically supplied as sterile solutions in a bottle with a rubber septum closure. To maintain sterility, aseptic techniques should be used when withdrawing solution and the rubber septum closure should not be removed.

The separation principle of using density gradient media is summarized below, as one example. Mononuclear cell isolation using Ficoll-Paque separation media is based on a methodology established through the extensive studies of Bøyum. Defibrinated or anticoagulant-treated blood is diluted with an equal volume of a balanced salt solution, layered carefully over Ficoll-Paque product (without intermixing) and centrifuged for 30 to 40 min. Differential migration of cells during centrifugation results in the formation of layers containing different cell types: The bottom layer contains erythrocytes, which have been aggregated by Ficoll PM400 and therefore sediment completely in the Ficoll-Paque density gradient media layer. The layer immediately above the erythrocyte layer contains mostly granulocytes, which at the osmotic pressure of the Ficoll-Paque media solution, attain a density high enough to migrate through the Ficoll Paque media layer. At the interface between the plasma and the Ficoll-Paque layer, mononuclear cells are found together with other slowly sedimenting particles (e.g., platelets) with low density.

Several factors are known to contribute to the success of density media based cell separation. During centrifugation, cells in the blood sample sediment towards the blood/Ficoll-Paque media interface, where they come in contact with the Ficoll PM400 present in Ficoll-Paque products. Red blood cells are efficiently aggregated by this agent at room temperature. Aggregation increases the rate of sedimentation of the red cells, which rapidly collect as a pellet at the bottom of the tube, where they are well separated from mononuclear cells. Granulocytes also sediment to the bottom of the Ficoll-Paque media layer. This process is facilitated by an increase in their densities caused by contact with the slightly hypertonic Ficoll-Paque media. Thus, on completion of centrifugation, both granulocytes and red blood cells are found at the bottom of the tube, beneath the Ficoll-Paque product. Lymphocytes, monocytes, and platelets are not dense enough to penetrate into the Ficoll-Paque media layers having densities of 1.077 and 1.084 g/ml. These cells therefore collect as a concentrated band at the interface between the original blood sample and the Ficoll-Paque products having densities of 1.077 and 1.084 g/ml. This banding enables the mononuclear cells to be recovered with high yield in a small volume with little mixing with the Ficoll-Paque media. When Ficoll-Paque PREMIUM 1.073 is used, some lymphocytes with densities >1.073 will enter the Ficoll-Paque media layer and the resulting cell preparation will be enriched for lower density cells like mesenchymal stromal/stem cells and monocytes. Washing and centrifuging the harvested cells subsequently removes platelets, any contaminating Ficoll-Paque media, and plasma. The resulting cell suspension then contains highly purified, viable lymphocytes, monocytes, mesenchymal stromal/stem cells, and is suitable for further studies.

The manufacturer of Ficoll-Paque recommends the following as the standard method for Ficoll Separation. Cell separation using Ficoll-Paque products can be carried out over a wide range of blood sample volumes. With its high yield, this method can be adapted to the processing of very small amounts of blood, such as may be obtained from children. For maximum reproducibility of separation, it is recommended that a standardized procedure be used. The following procedure with Ficoll-Paque PLUS is recommended for separation of normal blood samples. Simple changes can easily be made to suit a particular centrifugation system. The same procedure is recommended when separating cells using Ficoll-Paque PREMIUM, Ficoll-Paque PREMIUM 1.084, and Ficoll-Paque PREMIUM 1.073. To standardize the technique, blood volume and diameter of the centrifuge tube should be chosen first. These factors determine the height of the blood sample in the tube and consequently the centrifugation time. Increasing the height of the blood sample in the tube increases red cell contamination. The separation is, however, not appreciably affected by changing the diameter of the tube. Hence a larger volume can be separated with the same degree of purification in a tube of larger diameter if the height of the blood sample in the tube and the separation time are kept constant. The yield and degree of purity of the mononuclear cells depend to a considerable extent on the efficiency of red cell removal. When erythrocytes in whole blood are aggregated, some mononuclear cells are trapped in the clumps and therefore sediment with the erythrocytes. This tendency to trap mononuclear cells is reduced by diluting the blood. Dilution gives a better yield of mononuclear cells and reduces the size of the red cell clumps. Aggregation of erythrocytes is enhanced at higher temperatures (37° C.), which consequently decreases the yield of mononuclear cells. At lower temperatures (4° C.); however, the rate of aggregation is decreased but the time of separation is increased, which also decreases the yield of mononuclear cells. A compromise temperature of 18° C. to 20° C. gives optimal results. Larger volumes of blood may be processed with the same efficiency of separation by using centrifuge tubes of increased diameter while maintaining approximately the same heights of Ficoll-Paque media (2.4 cm) and blood sample (3.0 cm) as in the standard method described below. Increasing the tube diameter does not affect the separation time required.

Below is a specific procedure for the isolation of mononuclear cells using density gradient media.

A. Preparation of the Blood Sample

Fresh blood should be used to ensure high viability of isolated mononuclear cells. Prepare the sample at 18° C. to 20° C.

1. To a 10 ml centrifuge tube add 2 ml of defibrinated or anticoagulant-treated blood and an equal volume of balanced salt solution (final volume 4 ml).

2. Mix the blood and buffer by inverting the tube several times or by drawing the mixture in and out of a pipette.

B. Loading of the Centrifuge Tube

1. Invert the Ficoll-Paque media bottle several times to ensure thorough mixing. For withdrawal of Ficoll-Paque media by syringe: Snap-off the polypropylene cap and insert the syringe needle through the septum.

2. Add Ficoll-Paque media (3 ml) to the centrifuge tube.

3. Carefully layer the diluted blood sample (4 ml) onto the Ficoll-Paque media solution. Important: When layering the sample do not mix the Ficoll-Paque media solution and the diluted blood sample. As explained below, with the vial, system and method of this invention, this precaution is more easy and fully taken.

C. Stratification of Blood Components based on Density Using Centrifugation

1. Centrifuge at 400 g for 30 to 40 min at 18° C. to 20° C. (centrifuge brake should be turned off).

D. Extraction of Stratified Components from Centrifuge Tube

1. Draw off the upper layer containing plasma and platelets using a sterile pipette, leaving the mononuclear cell layer undisturbed at the interface. The upper layer, which contains the plasma, may be saved for later use.

2. Transfer the layer of mononuclear cells to a sterile centrifuge tube using a sterile pipette.

E. Washing the Cell Isolate

1. Estimate the volume of the transferred mononuclear cells. Add at least 3 volumes (~6 ml) of balanced salt solution to the mononuclear cells in the centrifuge tube.

2. Suspend the cells by gently drawing them in and out of a pipette.

3. Centrifuge at 400 to 500×g for 10 to 15 min at 18° C. to 20° C. Note: A centrifugation at high speed increases the mononuclear cell recovery. However, if it is important to also get rid of platelets a lower centrifugation speed is recommended (60 to 100×g).

4. Remove the supernatant.

5. Resuspend the mononuclear cells in 6 to 8 ml balanced salt solution.

6. Centrifuge at 400 to 500×g (or 60 to 100×g for removal of platelets) for 10 min at 18° C. to 20° C.

7. Remove the supernatant.

8. Resuspend the cell pellet in media appropriate for the application.

From the description above, it is apparent that the current procedures include steps where the blood is open to the atmosphere (e.g. various steps involving removing constituents by pipette from a centrifugation tube) and must therefore be performed in biosafety cabinets so as to reduce the risk of inadvertent microbial contamination. It is also evident that operator skill to perform cell separation is required particularly for the loading of the centrifuge tube with the density gradient media and adding the blood so as to avoid intermingling of the two fluids. In addition, considerable skill is required for an operator to fully extract the (typically very thin) isolated mononuclear cell band. Despite these limitations which have been known for more than 40 years, no alternative apparatus and method has been created to overcome all of these technical shortcomings of this common laboratory technique.

Ongoing advances in medicine, biochemistry and molecular biology allow researchers and clinicians to treat and diagnose diseases using cells and proteins purified from biological fluids. Despite this increasing importance, the methods of performing purifications of cells and proteins are time consuming, laborious and often introduce risk of microbial contamination of the purified product. Accordingly, to preserve the integrity of specimens for therapy and analysis, new techniques and apparatus are needed to ensure accurate and reproducible purifications that require less operator skill results, faster to perform, non-laborious and maintain the purified product free of microbial contaminants without the need for biosafety cabinets which are expensive and not available at the point of care.

SUMMARY OF THE INVENTION

With this invention a centrifugation vial, and associated system and method are provided to address many of the problems with cell separation from blood in the prior art. The vial, system and method of this invention could also be used for separation of other multi-constituent mixtures, other than blood, whether the mixture is a bodily fluid mixture or some other biological fluid mixture or non-biological fluid mixture. The present invention can be used for the separation of components of a biological fluid in a suspended medium to obtain cells, organelles, exosomes or macromolecules contained in multi-component biologic fluids including bone marrow, whole blood, peripheral blood, urine, phlegm, synovial semen, milk, saliva, mucus, sputum, exudates, cerebrospinal fluid, amniotic fluid, cord blood, intestinal fluid, cell suspensions, tissue digests, tumor cells containing cell suspensions, microbe containing cell suspensions, radiolabeled cell suspensions and cell culture fluid which may or may not contain additional substances (e.g., anticoagulants to prevent clotting).

The vial has an elongate form bounded laterally by a sidewall. This sidewall is collapsible at least partially, so that a volume of the vial inboard of the sidewall can be adjusted, and especially reduced. To achieve such collapsibility of the sidewall, some portion of the vial is flexible in form, either the sidewalls themselves or portions of the vial adjacent to the sidewalls, which allow the sidewalls to move toward and away from each other.

At a minimum, the vial has a first geometric shape which reversibly changes to a second geometric shape that has a lesser volume than the first geometric shape, during removal of a fraction of fluid contained within the vial. The vial is typically circular in cross-section, but could have other cross-sectional shapes. With the sidewalls being collapsible, the cross-sectional shape, and especially cross-sectional area is adjusted when such collapsing occurs. The volume of the vial is generally the product of the cross-sectional area of the vial (or at least an average thereof if it has an irregular cross-sectional area) and the length of the elongated vial. If the cross-sectional area is reduced by collapsing of the sidewall, then the volume of the vial is reduced.

To facilitate the vial geometric shape change and volume reduction, such as by sidewall collapse, in one embodiment the vial is composed of a flexible material selected from a list including low density polyethylene plastic, rubber, latex, poly chloroprene, nylon (including nylon fabric) and aluminized plastic, and with the vial walls, such as the sidewalls having a thickness between 0.2 and 2.0 millimeters. The vial walls are preferably transparent (or at least translucent) to allow visual inspection of fluid movement and location/movement of any boundaries between differing layers within the vial, such as during loading and extraction steps. In one embodiment, flexibility is focused or exclusive to the sidewall of the vial, with top and bottom regions of the vial (or a bulb at the bottom of the vial) being made of non-flexible (or less flexible) material (e.g. top and bottom caps), that are joined together, such as by a plastic tube that is flexible for the sidewall with or without having rigid supports connecting such top and bottom caps.

Other details of the vial could vary in different embodiments, such as to facilitate collapsibility in various different embodiments, and to provide other vial functional performance attributes. For instance, the vial is typically at least translucent, if not transparent, so that interior contents can be viewed, but could alternatively be opaque. A vial typically includes a floor at a first end opposite a second end, with the first and second end spaced apart by an elongate length of the vial. An interface is provided at the second end (or at least spaced from the first end) through which interface fluids can be introduced into and removed from the interior of the vial. Optionally, a processing element can be provided, typically near the interface, which could be in the form of some type of filtration element or be in the form of a one-way valve or other valve or otherwise provide some processing of fluids passing through the processing element or coming adjacent to the processing element. In many embodiments, no such processing element would be included.

In many desirable embodiments, the vial includes a bulb adjacent the first end and a neck extending from the bulb toward the second end. The bulb and neck can be similar to each other, except that the bulb is generally characterized by having a larger cross-sectional area than the neck. In many embodiments the collapsible sidewall is only extending along the bulb, and does not extend along the neck. A transition, such as a conical transition, can be provided between the bulb and the neck which defines an area where the cross-sectional area of the vial transitions from the cross-sectional area of the bulb into the cross-sectional area of the neck. The length of the bulb and the length of the neck can vary in different embodiments, such as with the bulb being longer than the neck or with the neck being longer than the bulb, with different vials optimized to perform different fluid mixture separation processes most effectively.

To achieve sidewall collapsibility, most preferably a strength of the vial is less than a strength of atmospheric pressure. Thus, applying suction to an interior of the vial, this causes the sidewalls to collapse inward. Such a suction applied to the interior of the vial would typically occur by attaching a syringe to the interface and then working the plunger of the syringe to draw a vacuum on the interior of the vial, and to cause sidewall collapsing of the vial. As an alternative to such a syringe, or in addition thereto, the sidewall could be collapsed by suction caused by a pump, or caused by applying squeezing forces external to the sidewall of the vial and inward on the vial, or some combination of such sidewall collapsing methodologies.

In one embodiment, while the vial is formed to have strength characteristics insufficient to resist atmospheric forces, the vial is strong enough to undergo centrifugation forces without significant (e.g. a few percent) elongation of the vial during use within a centrifuge, such as a centrifuge which might apply up to about 500 gees acceleration to the vial. Thus, the vial is strong enough to resist centrifugation forces without appreciable elongation or other deformation, but not so strong that it resists sidewall collapse when atmospheric pressure (or other) forces are applied differentially between an interior of the vial and an exterior of the vial. In another embodiment, the vial is not sufficiently strong to avoid appreciable deformation when undergoing centrifugation, and instead a support cup is utilized to keep the vial from experiencing undesirably excessive deformation when undergoing centrifugation.

One support cup for holding the centrifugation vial in a manner generally maintaining its shape and cross-sectional area has a length generally matching a length of the vial and a width and cross-sectional area generally matching a cross-sectional area of an exterior surface of the vial. The vial can then be placed within such a support cup and the support cup can be formed of a high strength and rigid material sufficiently strong to withstand forces associated with centrifugation, such as up to 500 gees, or more. The support cup would have a bottom which would reside adjacent to a floor of the vial, and preferably have a contour matching the floor of the vial, for intimate support of the floor of the vial, such as during centrifugation. The collapsible sidewall of the vial, or in many embodiments just the bulb of the vial, is preferably directly adjacent to a wall of the support cup which extends away from the bottom of the support cup and toward an entry at an end of the support cup opposite the bottom. This wall provides lateral support to the collapsible sidewall of the vial, so that centrifugation forces do not cause the collapsible sidewall to bulge laterally outwardly any appreciable amount during centrifugation. Typically the neck of the vial is sufficiently strong to not require support. However, a support structure could be inserted into the support cup and surrounding the neck, if needed for further support of the neck. Furthermore, portions of the vial, such as a processing element or interface at an end of the vial opposite the floor and at the second end thereof could be further supported by an optional support interfacing with the support cup but holding portions of the vial adjacent to the second end of the vial securely in place and supported against forces associated with centrifugation.

The vial and support cup, as well as optional support, together provide major parts of a system of this invention featuring a collapsible centrifugation vial. A further element of such a system include some form of centrifuge. Any known centrifuge in the prior art, or developed in the future, could be utilized for centrifugation of fluid mixtures within the vial of this invention. One typical centrifuge includes a motor with a rotating output shaft which rotates cupholders relative to this output shaft. The cupholders can hold a rim of at least one support cup opposite a bottom, and with a vial inside of the support cup.

The cupholders in one such centrifuge are mounted through hinges to the output shaft. Thus, the cupholders can be oriented to allow a support cup and/or centrifugation vial to be inserted vertically down into the cupholder when the centrifuge is not operating. Then, when the centrifuge motor begins to rotate the output shaft, the cupholders pivot about the hinges to rotate about a vertical axis and for the vial (or multiple vials) to extend horizontally with the second end including the floor of the vial most distant from the rotational axis of the centrifuge. When centrifugation is complete, and the rotation of the centrifuge slows down to a stop, the vials very gradually pivot about the hinges back down to a vertical orientation without disturbing the different layers of constituents separated from the mixture within the vial. The vial can then be removed vertically up out of the cupholders, further without disturbing constituent layers within the vial. Other forms of centrifuges could be utilized as an alternative utilizing known techniques.

General methods of this invention involve placing a mixture into the vial, followed by placing the vial into the centrifuge, with or without a support cup if needed. The centrifuge is then operated to separate constituent fluids from the fluid mixture within the vial. In various different methodologies other constituents can be added to the mixture being separated, to facilitate separation of various different constituents. For instance, when different fractions of blood are being separated from each other, medium density separation fluids can be utilized which allow for greater separation of blood fractions from each other. In other methods, water absorbing beads can be utilized or beads which absorb various different constituents preferentially over others can be utilized to further assist in the separation process. Other portions of methods useful with this invention can differ based on the particular processing element either associated with the vial or attached to the vial through the interface at the second end of the vial. Multi-step methods are also disclosed herein utilizing one or more centrifugation vials of different types with at least one of the vials benefiting from having a collapsible sidewall.

OBJECTS OF THE INVENTION

Accordingly, a primary object of the present invention is to provide a centrifugation vial which can more easily separate constituents out of a fluid mixture.

Another object of the present invention is to provide a centrifugation vial which can separate constituents out of a fluid mixture with a lesser risk of microbial contamination of purified products.

Another object of the present invention is to provide a centrifugation vial which can preserve the integrity of specimens for therapy and/or analysis, and to enable accurate and reproducible purifications.

Another object of the present invention is to provide a centrifugation vial which can be utilized by operators with less skill to still achieve high purity separation of a multiple constituent mixture.

Another object of the present invention is to provide a method for separation of constituents within a multi-part mixture without requiring utilization of biosafety cabinets.

Another object of the present invention is to provide a method for separation of constituents from blood or other bodily fluids at a point of care which provides high purity separation constituents in a timely manner for therapeutic use.

Another object of the present invention is to provide a method for separation of constituents from a fluid mixture where fluids are transferred into and out of a centrifugation vial with the vial having a collapsible sidewall to minimize turbulent flow of fluids being placed into or removed from the vial, and potential associated effects of inappropriate handling.

Another object of the present invention is to provide a centrifugation vial which includes a larger cross-sectional area bulb portion and a smaller cross-sectional diameter neck portion and which bulb portion includes a collapsible sidewall so that constituents of a mixture within the vial, after centrifugation can be transitioned from the bulb portion into the neck portion for better identification of target constituents for effective extraction thereof from the vial.

Another object of the present invention is to reduce the time and skill required as well as to reduce the risk of inadvertent microbial contamination of liquids during the steps of introducing and extracting materials into and out of a centrifuge apparatus.

Another object of the present invention is to provide a vial with a collapsible sidewall for use in processing biologic fluids for purposes such as diagnosing, treating, curing and prevention of diseases in humans, animals and plants. The present invention is especially useful for regenerative medicine applications in which the patient's own body fluids are used to prepare therapeutic compositions including platelet rich plasma, stem cell concentrates, exosome concentrates and protein concentrates including concentrates of fibrinogen, alpha-2-macroglobulin, cytokines and growth factors. The present invention is especially useful for diagnostic procedures employing cytometric procedures and devices to measure the characteristic of cells including cell size, cell number, cell morphology (shape and structure), cell cycle phase, DNA content and the existence or absence of specific proteins on the cell surface or in the cytoplasm. It facilitates these processes by, among other things, providing a faster, simpler and more reliable method to isolate purified cells and macromolecules. The present invention is particularly adept at depletion of red blood cells from heterogeneous cell mixtures.

Other further objects of the present invention will become apparent from a careful reading of the included drawing figures, the claims and detailed description of the invention.

BRIEF DESCRIPTION OF THE DRAWINGS

FIG. 1 is a side elevation view of a basic centrifugation vial according to this invention.

FIG. 2 is a detail of a portion of that which is shown in FIG. 1 and featuring a vial with a sidewall having variable thickness to provide different strength characteristics to different portions of the vial.

FIG. 3 is a detail of a portion of that which is shown in FIG. 1 and featuring a sidewall having different material characteristics at different portions of the sidewall to facilitate sidewall collapsibility.

FIG. 4 is a detail of a portion of that which is shown in FIG. 1 and featuring a zone of differential weakness or strength on a portion of the sidewall which facilitates collapse either at a zone of relative weakness or away from a zone of relative strength.

FIG. 17 is a side elevation view of a further alternative embodiment particle filter vial which is shown including SAP water extraction beads within the vial for use in methods and in embodiments where water extraction is beneficial for simplification of separation procedures.

FIG. 18 is a side elevation view of a further alternative sterile filter vial including a filter as an intermediate processing element associated with the vial.

FIG. 19 is a side elevation view of a further alternative vial including elongate tubing for convenience in handling of the fluid mixture before certification and extraction of constituent fluids after centrifugation.

DESCRIPTION OF THE PREFERRED EMBODIMENT

Figure 5:
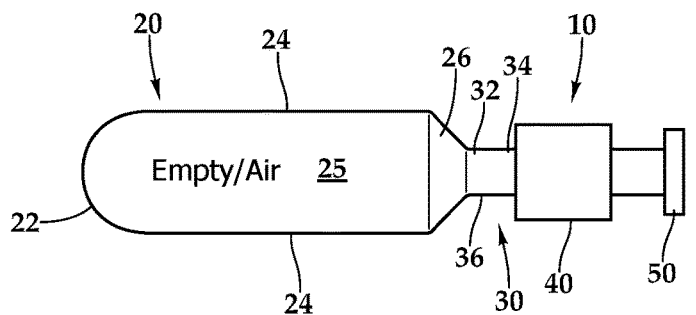
FIGS. 5-9 are side elevation views similar to that shown in FIG. 1, and illustrating a series of steps in loading the centrifugation vial according to this invention and utilizing the centrifugation vial within a centrifuge for separation of constituents of a fluid mixture into different stratified layers, according to one method of this invention and utilizing a system of this invention including the centrifugation vial, as well as an optional support cup, within centrifuge equipment.

Referring to the drawings, wherein like reference numerals represent like parts throughout the various drawing figures, reference numeral 10 (FIGS. 1-4) is directed to a vial which can be used for centrifugation of a multiple constituent mixture, such as blood B. The vial 10 features a collapsible sidewall 24 to facilitate smooth and simple loading and extraction of the centrifugation vial 10. A support cup 60 can optionally be provided to support the vial 10 during centrifugation. Various alternative embodiments of the vial 10 are optimized for use in particular specialized mixture separation procedures.

Figure 8:
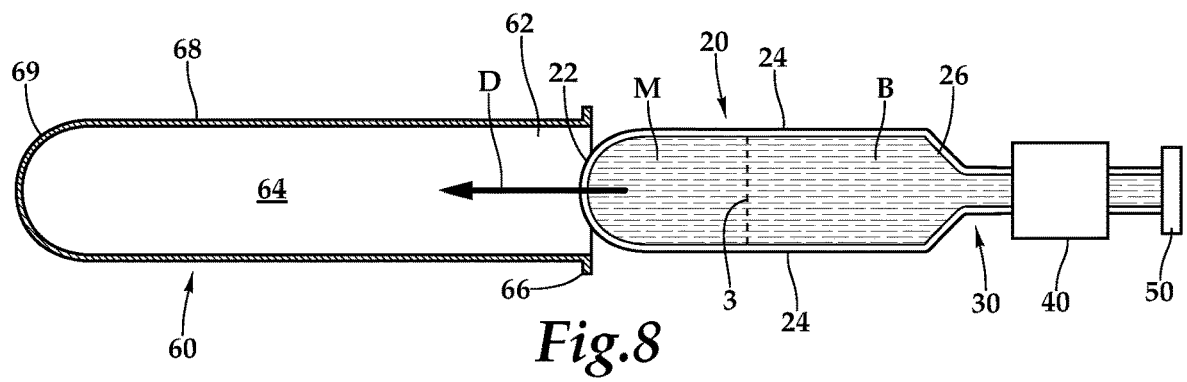

In essence, and with particular reference to FIG. 1, basic details of the vial 10 are described, according to one embodiment, provided as a somewhat generic typical example. The vial 10 in this embodiment includes a bulb 20 at a first end and a neck 30 extending from the bulb 20 to a second end opposite the first end. The bulb 20 features a collapsible sidewall 24 which is able to move laterally (along arrow A of FIG. 1) to reduce a cross-sectional area of at least the bulb 20 portion of the vial 10. The neck 30 extends to an interface 50 with an optional processing element 40 along the neck 30, or with such a processing element 40 attached through the interface 50 beyond the second end of the vial 10. A support cup 60 (FIGS. 8 and 9) is optionally provided into which the vial 10 is inserted during centrifugation. The support cup 60 is sized to support the vial 10 structurally to resist centrifugation forces, should the vial 10 be insufficiently strong to otherwise withstand these forces. A centrifuge 70 is also disclosed for use along with the vial 10 and optional support cup 60 as part of a system for centrifugation, also featuring the vial 10 with a collapsible sidewall 24. Various methods of use also disclosed herein.

More particularly, and initially describing the vial, system and a method of this invention according to more generic vials 10 featuring a collapsible sidewall 24, basic details of the vial 10, system and method are described. The method is described according to various different methods which illustrate separation of blood into different constituent fractions. Other methodologies could also be provided for separation of other bodily fluids or other biological fluids, or for separation of non-biological fluids into different constituents having different densities.

The present invention provides a new centrifuge system. A method for use of the new centrifuge system is also provided for purification of heterogeneous mixtures of particles differing in size and/or density. The assembly is particularly useful for purifying mixtures in which the target particle (particle which is desired to be purified) has a lighter density than a more preponderant non-target particle. For example, the assembly and method can be used for the separation of platelets, stem cells or leukocytes away from red blood cells in peripheral blood, cord blood or bone marrow aspirate on one embodiment. Additionally, the present invention is particularly suitable for the separation of low density acellular fluid fractions formed after centrifugation.

The present invention is a liquid-receiving centrifuge apparatus container with an interior volume that is generally cylindrical in shape manufactured of flexible plastic such as low density polyethylene and having two distinctive regions: a first collapsible elastic bulb region having a larger diameter that is in communication with a second more rigid neck region which is smaller in diameter that serves as a conduit member. The orientation of the container at the time of centrifugation is with the bulb region oriented such the conduit member is proximate to the rotor spindle and the bulb is distal. The bulb is designed such that when a vacuum is applied by removal of liquid or gas from the apparatus its walls will preferentially collapse in the bulb region instead of the neck region and do so in a way that is proportional to the vacuum applied to the apparatus and, preferably, is sufficiently elastic that it will return to its original shape when the vacuum is replaced by the introduction of a liquid or gas. At least the bulb region is filled with liquid during centrifugation and preferentially both the bulb and neck (also called a stem) region are filled with liquid during the time of centrifugation.

Figure 16:
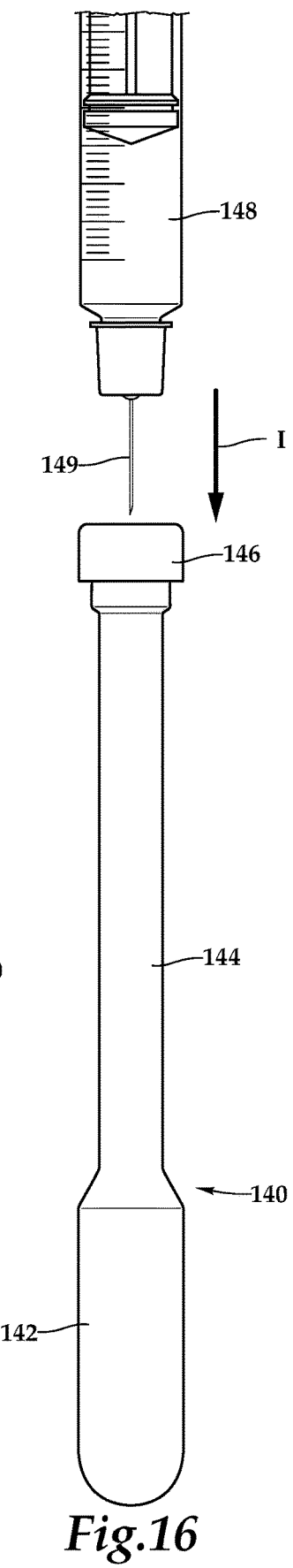
FIG. 16 is a side elevation view of a further alternative embodiment vial featuring a long neck and with an interface in the form of a septum, such as that which can be penetrated by a needle attached to a syringe, for access and placement of fluids into and out of such a vial.

In one embodiment, the inlet of the neck region of the device is hermetically sealed at its second end by means of an injection port having a septum by which needle can penetrate for the purpose of removal of air from the device and for the sterile ingress and egress of fluids by means of a syringe with an attached needle (see FIG. 16 for instance). In another embodiment, the opening of the neck region is hermetically sealed at its distal (to the bulb) end by means of pre-slit swabbable valve for the sterile ingress and egress of fluids by means of a syringe without need for a needle.

Due to the elasticity of the bulb region, it is preferred to provide the elastic bulb with mechanical support during the time of centrifugation, to prevent distortion of the bulb shape or breakage and to maintain the orientation of the stem region's proximity to the centrifuge spindle relative to the bulb region during centrifugation. In one embodiment, mechanical support of the elastic bulb region is provided through a support cup 60 that is comprised of a tube of sufficient size to contain the bulb and stem region of the centrifuge region, with a sealed lid having a hole in the lid for the stem region to be adjacent thereto, such that an injection port with septum or a pre-slit swabbable valve can be external to the tube but still be attached to the stem region, so as to enable the ingress and egress of liquids and particles in an out of the bulb and stem regions of the device.

An important and unexpected observation made during experimentation was that the contents of the stem region can be removed by applying a vacuum force to the hermetically sealed container sufficient to cause the preferential contraction of the bulb region but not the stem region of the container, wherein said contraction of bulb results in the displacement of the fluid contents of the stem region out of the container with minimal mixing with the bulb contents. As a result, the density stratification that is achieved within the stem during centrifugation remains intact even when the force causing the displacement of liquid out of the container is derived from the collapsing bulb. It would be expected that substantial mixing would have occurred, but this was not the case when observed upon experimentation.

To take advantage of this method for extracting fluids out of the container after the intended stratification has been achieved by centrifuging the liquid for appropriate time and force, a tubing apparatus for the extraction of cell fractions from the liquid-receiving centrifuge apparatus is disclosed which in the case of a device sealed with an injection port having a septum is comprised of a needle attached to a tube, wherein the tube contains a duckbill check valve device that allows flow unidirectionally away from the centrifuge container and the tube ends in a female Luer enabling the attachment of a syringe via a male Luer. By pulling back the plunger of the syringe in a careful way, the gradual movement of the contents of the centrifuge tube occurs into the needle, through the check valve, through the tubing beyond the check valve (but cannot return to the container due to the orientation of the check valve), and eventually entering into the attached syringe. Visual inspection of the preferably transparent tubing which is preferably a very small bore tubing (e.g., 1.8 mm) allows cessation of withdrawal fluids when appropriate to prevent contamination of the contents of the harvest syringe.

Similarly, the present invention also discloses a tubing apparatus for the extraction of fractions from the centrifuge apparatus disclosed wherein the stem region is hermetically sealed using a pre-slit swabbable valve using a tubing set that ends in a male Luer connected to a tube wherein there is a duckbill check valve device that allows flow unidirectionally away from the centrifuge apparatus and the tube ends in a pre-slit swabbable valve that enables the attachment of a syringe via its male Luer. The syringe transmits a vacuum force through the tubing and through the stem region to remotely cause the preferential collapse of the bulb region to thereby force the fluid in the stem region to enter the tubing and ultimately to enter the harvesting syringe which is the source of the vacuum.

Another unexpected but useful finding was observed during experimentation regarding the introduction of liquids having different density into the centrifuge tube container disclosed above. The general preferred method of introducing a fluid into the hermetically sealed centrifuge tube is to first withdraw a vacuum sufficient to evacuate air out of the device and result in collapse of the elastic bulb region. Upon achieving collapse, the syringe is orientated so that its fluid contents are in contact with the exit of the syringe and thereby are sucked into the container to relieve the vacuum. Therefore, the preferred method of introducing fluids into the disclosed centrifuge tube is comprising of first removing gas contained within the centrifuge apparatus and replacing at least a part of the removed gas a with a liquid.

It was very surprising to learn upon experimentation that two different liquids could be successively added in the above manner by first adding the liquid with higher density and then adding the liquid with lower density and to observe the two fluids were not intermingled. This provides an important improvement to the process of combining Ficoll-Paque (density 1.073) with whole blood (density 1.04) without intermingling the two fluids as is required in the previously reviewed method of performing density gradient centrifugation. The technique described above requires considerably less time and skill than previously disclosed methods and is a functionally closed system, so that the risk of inadvertent microbial contamination is greatly reduced and very importantly without the need of a major piece of laboratory equipment, known as a "biosafety cabinet," being required.

In summary, a method of introducing fluids into the disclosed device consists of removing air from the centrifugation container to create a vacuum which preferentially collapses the bulb region but not the stem region and then relieving the vacuum by insertion of a liquid to restore the shape of the bulb to its non-compressed form. In one embodiment, a method of harvesting fractions from the disclosed centrifuge container comprises attaching a tubing set and then withdrawing fluid into a syringe using the attached tubing as the conduit.

The present centrifuge apparatus can be designed so as to be suitable for high resolution purification of a heterogeneous mixture. This high resolution purification is achieved by selecting a centrifuge apparatus wherein the total volume to be centrifuged can be fully contained in the combined volumes of the bulb and the stem regions of the centrifuge apparatus. For high resolution purification, the relative size of the bulb region to the stem region is carefully selected such that after carefully selected centrifugation conditions using optimized time and centrifugal force, the target particles to be purified will come to reside in the stem region and the higher density non-target particles or high density liquid will reside both in the bulb and in the lower part of the stem region.

The volume of the bulb and the stem are selected based upon the material to be centrifuged as discussed below. In general, for high resolution separation, consideration is given to the volume of higher density material to be centrifuged and matching it to an apparatus having a bulb region of that volume and the apparatus having a stem volume sufficient to contain the target product, such that the target particle of purification becomes concentrated in the narrow stem region of the apparatus after centrifugation.

The ratio of the bulb size to the stem region is selected so that the compression of the bulb region will cause the target population particles to exit the stem region into a harvesting device, but not the higher density non-target particles. Although the bulb region can be compressed manually, it is preferable to compress the bulb remotely by the removal of air and liquid from the more rigid stem region by suction. This compression of the bulb results in the higher density particles moving upward into the stem region. It was an important experimental observation that this movement of higher density fluid into a region occupied by a lower density fluid region occurred without the intermingling of the density layers such that the stratification according to particle density and size achieved during the centrifugation was maintained during the extraction process. This laminar (or otherwise non-mixing) flow of fluids was essential for the present invention to be used in high resolution particle separation, because if intermingling of the layers had been observed to occur, the ability to achieve high resolution cell separation would have been lost. The achievement of high resolution cell separation can thus be achieved by the selection of one or more of the bulb region volume, length and diameter, the stem region volume, length and diameter and the proportion of the bulb region volume to the stem region volume, to match the composition of the mixture to be centrifuged in terms of the volumes of high density particles and low density particles.

The present invention is particularly suited when the low density particles are the target particles and the high density particles are non-target particles to be purified. For example, mononuclear cells have a lower density and would be an excellent target population to be purified from higher density red blood cells. The volume of red blood cells in a cell suspension is measured by hematology analyzers and is reported as the hematocrit of the blood mixture. During centrifugation, it is possible to pack red cells to a hematocrit of greater than 50% and even up to 85% if enough centrifugation force is applied. Therefore, the volume to be occupied by the packed red blood cell fraction can be estimated with accuracy once the hematocrit of a cell suspension, the centrifuge force (time and speed) force to be employed and the amount of the cell mixture to be centrifuged are known. The bulb size can be selected so that it will be filled with the packed red blood cells and the stem region volume selected so that it will hold the balance of the cell mixture volume. It is desirable to select cell mixtures in which the target cells can be ejected from the centrifuge apparatus after stratification into density layers by centrifugation, by applying a compressive force to the bulb region. Buffy coat preparations are particularly well suited for purification with the present invention. A preferred compressive force is the introduction of a vacuum in tubing hermetically connected to the centrifuge apparatus, wherein a controlled vacuum is created by pulling back on a syringe attached hermetically to the tubing. Other vacuum sources could be used as an alternative, or the bulb could be compressed, either manually or by some compression assembly that is either automated or not in its use.

It is envisioned that a specific centrifuge apparatus will be constructed with bulb and stem regions adjusted for specific cell separation needs with consideration given to the cell composition of the mixture, the purpose of the separation, and the centrifuge force to be applied.

In general, there will two basic types of centrifuge apparatus geometries employed for many applications. For high resolution purification, the centrifuge apparatus will employ a bulb region having approximately the same volume as the stem region designated herein as Type I centrifuge apparatus. For low resolution purifications, the centrifuge apparatus will employ a bulb region having at least three times the volume of the stem region, designated herein as a Type II centrifuge apparatus.

The following comments apply for both Type I and Type II centrifuge apparatus. The construction of the tube is preferably one-piece composed of polyethylene plastic that is inert to biological fluids. In a preferred embodiment the stem is hermetically sealed with an injection site port that can be penetrated with a needle. Alternatively, injection site port is a swabbable pre-slit transfer valve that is opened by the attachment of a male Luer to the valve and closes upon removal of the male Luer to create a functionally closed system so as to avoid microbial contaminants inadvertently from entering into the centrifuge tube. The valve is disinfected prior to each use by contacting it with an alcohol (or similar) disinfectant. Alternatively, the stem can be sealed with an injection site port that employs a needle to penetrate a septum to access the bore of the centrifuge device. In preferred embodiments, the injection site and the stem of the centrifuge tube are connected so as to create a hermetic seal so that withdrawal of air from the centrifuge results in the creation of a vacuum within the centrifuge tube preferentially causing the bulb portion of the tube to collapse while the shape of the stem portion is not appreciably changed.

For applications not involving high resolution separation of particles populations such as preparing a buffy coat fraction from whole blood, cord blood or bone marrow aspirate, for cell washing or for reducing the amount of dimethylsulfoxide (DMSO) in a cryopreserved cell product, a Type II Centrifuge Apparatus is generally preferred. The bulb size is selected in which essentially all of the cells pelleted by centrifugation will reside in the elastic bulb after completion of the centrifugation process. After centrifugation to pellet the cells in the bulb, the bulb is compressed as discussed below to force the supernatant fluid (platelet poor plasma, wash solution or DMSO to exit the apparatus without loss of the cellular fraction.

The bulb region may be supported by being sized to fit snugly into the centrifuge bucket employed during centrifugation or the bulb can be supported by a surrounding structure such as a centrifuge tube to provide mechanical support to the elastic bulb. For example, the stem region can be attached to the lid of a supporting centrifuge tube capable of withstanding centrifugal forces that will be used wherein a hole is made in the lid to allow the stem region to exit so as to have operator access to the interior of the centrifuge apparatus. Further, the bulb may be supported by filling the centrifuge tube with a liquid such as water to surround the bulb which will prevent breakage or distortion of the bulb during centrifugation. Alternatively, a dry system of mechanical support can be made of a shape complemental to the bulb by preparing a solid support molded (or otherwise formed) so that the bulb is substantially surrounded by the solid support structure at the time of centrifugation.

During centrifugation, the bulb portion of the device is oriented to be in the region of higher g meaning that is located farther away from the spindle of the centrifuge rotor as compared to the stem portion. To avoid breakage of the bulb during centrifugation, it is preferred to provide a physical support to the bulb region of the centrifuge tube. This support can be in in the form of a hard plastic shell in the general shape of the bulb or it can be in the form of a liquid including water surrounding the bulb during centrifugation.

The centrifuge device is used with a harvest tubing assembly which, in one embodiment, is comprised of a narrow tube. For instance, a 1.8 mm inner diameter and a 4.8 mm outer diameter and a length of 25 cm, and the tube is fitted with a male Luer enabling connection with the pre-slit valve of the centrifuge tube and other end having a female Luer enabling connection of a syringe. In more preferred embodiments, the tubing also contains proximate to the male Luer ending (or perhaps elsewhere) a one-way valve permitting flow away from the centrifuge tube. The female Luer ending in preferred embodiments comprises a pre-slit swabbable valve. The tubing can be of variable length and diameter, but it is advantageous to have a relatively small inner diameter such as 1.8 mm and an outer diameter of 4.8 mm. The length of the tubing can be variable, but a convenient length is 25.4 cm. A complete harvest tubing assembly therefore consists of a male Luer connected to a one-way valve connected to tubing connected to a pre-slit swabbable valve. The male Luer is used to connect to the centrifuge tube post-centrifugation and the pre-slit swabbable valve is used to attach to syringes used for harvesting fluid fractions from the centrifuge tube.

To extract fluid fraction after centrifugation, a vacuum is created in the centrifuge tube by withdrawing the plunger of the syringe to remove the air in the device causing collapse of the bulb, which forces the fluid contents of the bulb contents to enter the attached tubing. The lightest density fractions enter the harvest syringe first. The one-way valve prevents extracted material from being sucked back into the centrifuge apparatus which could potentially disrupt the stratification achieved during the centrifugation step due to mixing of lighter and heavier fractions which would be negative to the purification process.

Method and Device for Isolation of Mononuclear Cells from Small Volumes of Blood with the Use of Density Media.

Below is a step by step description of the improved procedure for the isolation of mononuclear cells using density gradient media employing the new centrifuge apparatus and harvest tubing assembly.

A. Selection of Centrifuge Apparatus

For the following procedure, a centrifuge apparatus is employed wherein the volume of the bulb region is 4.4 ml and the volume of the stem region is 3 ml.

B. Preparation of the Blood Sample

Fresh blood should be used to ensure high viability of isolated mononuclear cells. Prepare the sample at 18° C. to 20° C.

1. To a 10 ml syringe add 2 ml of defibrinated or anticoagulant-treated blood and an equal volume of balanced salt solution (final volume 4 ml).

2. Mix the blood and buffer by inverting the syringe several times.

C. Loading of the Centrifuge Apparatus

1. Invert the Ficoll-Paque media bottle several times to ensure thorough mixing. For withdrawal of Ficoll-Paque media using a second 10 ml syringe: Snap-off the polypropylene cap and insert the syringe needle through the septum.

2. Add Ficoll-Paque media (3 ml) to the second 10 ml syringe.

3. Swab the valve with alcohol to disinfect and then attach the second 10 ml syringe containing 3 ml of Ficoll-Paque.

4. Withdraw the plunger of the second 10 ml syringe to at least the 7 ml mark so to create a vacuum causing the bulb to collapse, and then orient the syringe to be above the centrifuge apparatus and release the plunger which will cause a portion of the Ficoll-Paque to leave the bulb. Repeat this process until all the Ficoll is in the bulb and the second syringe is empty.

5. Next attach the first syringe containing the blood and buffer mixture and again withdraw the plunger to create a vacuum in the centrifuge apparatus, pull the plunger back until the Ficoll fluid is approaching the swabbable valve and then slowly push downward on the plunger of the first syringe, filling the centrifuge apparatus with the blood mixture. This technique results surprisingly in the blood mixture not intermingling with the Ficoll which is the required outcome of combining the two liquids. It will be observed that the disclosed technique is a simpler method than prior art to achieve the combination of the two fluids without their becoming intermingled. This technique is also faster to perform than using a pipet to layer the diluted blood sample onto the Ficoll-Paque media solution and even more importantly avoids the need for a biosafety cabinet to maintain sterility of the samples.

D. Stratification of Blood Components by Centrifugation

Centrifuge the tube containing the blood and Ficoll fluid at 400 g of acceleration for 15 minutes at 18° C. to 20° C. (centrifuge brake should be turned off).

E. Extraction of Stratified Components from Centrifuge Tube

1. Swab the valve again with alcohol and then attach a complete harvest tubing set to the pre-slit valve of the centrifuge tube using the male Luer. Attach a third syringe to the other end of the tubing set which has a pre-slit one-way valve. Draw off the upper layer containing plasma and platelets using the third syringe, until the mononuclear cell layer are observed to enter the at least partially transparent tubing. The third syringe is then removed and replaced with a fourth harvest syringe, for the purpose of harvesting the mononuclear cell band. The fourth syringe has its plunger withdrawn, causing the mononuclear cells to travel into the syringe, as the bulb collapses (under pressure from the surrounding atmosphere as a vacuum is drawn on its interior by plunger withdrawal). The mononuclear cells are thus harvested into the fourth syringe. The third syringe containing the plasma may be saved for later use.

2. Remove the fourth syringe from the harvest tubing set and transfer the mononuclear cells in the fourth harvest syringe to a sterile centrifuge tube.

E Washing the Cell Isolate

1. Estimate the volume of the transferred mononuclear cells. Add at least 3 volumes (~6 ml) of balanced salt solution to the mononuclear cells in the centrifuge tube.

2. Suspend the cells by gently drawing them in and out of a pipette.

3. Centrifuge at 400 to 500×g for 10 to 15 min at 18° C. to 20° C. Note: A centrifugation at high speed increases the mononuclear cell recovery. However, if it is important to also get rid of platelets a lower centrifugation speed is recommended (60 to 100×g).

4. Remove the supernatant.

5. Resuspend the mononuclear cells in 6 to 8 ml balanced salt solution.

6. Centrifuge at 400 to 500×g (or 60 to 100×g for removal of platelets) for 10 min at 18° C. to 20° C.

7. Remove the supernatant.

8. Resuspend the cell pellet in media appropriate for the application.

The above method is suitable for the isolation of mononuclear cells which include lymphocytes, monocytes and stem cells but not for isolating granulocytes (neutrophils, basophils and eosinophils). The procedure for isolation of granulocytes is described below.

1. Perform density gradient centrifugation using Ficoll-Paque media as described above (Steps A-D).

2. Replace the fourth syringe used for harvesting the mononuclear cell band with a 10 ml syringe attached to the Harvest Assembly and continue to draw off the upper layer of Ficoll-Paque media until the white cell layer of granulocytes and some red cells are observed to enter the tubing. At this time, the fourth syringe is replaced with a fifth 3 ml syringe which is used to collect between 1 to 2 ml of liquid which will be a mixture of granulocytes and red cells.

3. Transfer the 1-2 ml to a 50 ml centrifuge tube and lyse red blood cells with any red blood cell lysis solution of choice.

4. Centrifuge the granulocytes at 400 to 500×g for 10 to 15 min at 18° C. to 20° C.

5. Remove the supernatant.

6. Resuspend the granulocytes in 6 to 8 ml balanced salt solution.

7. Centrifuge at 400 to 500×g for 10 min at 18° C. to 20° C.

8. Remove the supernatant.

9. Resuspend the cell pellet in media appropriate for the application.

From the example above, it is apparent that the new centrifuge apparatus and method of use provides important improvements from past practices of using density media to separate mononuclear cells. These improvements include the obviation for the need of the procedure to be performed in expensive biosafety cabinets to reduce the risk of microbial contamination It is also evident that operator skill required to perform cell separation is reduced with the present invention particularly for the loading of the centrifuge tube with the density gradient media and the blood so as to avoid intermingling of the two fluids and in the extraction of the mononuclear cell band. Despite these improvements, the method of obtaining mononuclear cells using a density media is a long procedure principally due to the need to wash the isolated cells to remove the added Ficoll.

Method and Device for Isolation of Mononuclear Cells from Large Volumes of Blood with the Use of Density Media.

To achieve preparation of mononuclear cells from large volumes of peripheral blood with the use of density media, the centrifuge apparatus of the present invention was employed using the following method.

A. Selection of Centrifuge Apparatus

For the following procedure when Ficoll is employed, a centrifuge apparatus is employed wherein the volume of the bulb region is 4.4 ml and the volume of the stem region is 3 ml.

B. Preparation of a Buffy Coat Fraction

The buffy coat is the fraction of an anticoagulated blood sample that contains most of the white blood cells and platelets following centrifugation of the blood. Fresh blood should be used to ensure high viability of isolated cells. Prepare the sample at 18° C. to 20° C. The entire bulb can contain up to 60 ml of fluid. In this example, the top of the centrifuge apparatus is sealed with a pre-slit swabbable valve. Blood would be introduced using a 60 ml syringe by first aspirating out air from the bulb causing the bulb to compress. The compressed bulb would then be filled with blood to restore the bulb to its original shape. The centrifuge apparatus would be centrifuged for a sufficient period to stratify the blood into three layers: an upper platelet poor plasma layer, a middle buffy coat layer and a lower packed red cell layer. A sufficient centrifuge force is 7 minutes at 3,800 rpm in a Hettich Rotofix centrifuge, provided by HETTICH Instruments LP of Beverly, Mass. After centrifugation, a harvest tube assembly, as shown above, would be attached to the centrifuge tube apparatus. First the platelet poor plasma would be extracted using a 60 ml syringe and when cells are observed to enter the tubing, extraction of the platelet poor plasma would be considered completed and a 10 ml syringe would be attached to the harvest tubing assembly. At this point, 8 ml of buffy coat fraction would be harvested in the 10 ml syringe and would be used for the next step of high purity centrifugation resolution using a different shaped centrifuge apparatus of the present invention (volume of stem and bulb are more similar). The packed red blood cells layer remaining in the centrifuge apparatus is discarded.

C. Loading of the Centrifuge Apparatus with Ficoll and Buffy Coat

1. Invert the Ficoll-Paque media bottle several times to ensure thorough mixing. For withdrawal of Ficoll-Paque media using a 10 ml syringe: Snap-off the polypropylene cap and insert the syringe needle through the septum.

2. Add Ficoll-Paque media (3 ml) to the 10 ml syringe.

3. Swab the valve with alcohol to disinfect and then attach the 10 ml syringe containing 3 ml of Ficoll-Paque.

4. Withdraw the plunger of the 10 ml syringe to at least the 7 ml mark so to create a vacuum causing the bulb to collapse, and then orient the syringe so the Ficoll fluid is at the bottom of the syringe and slowly release the plunger which will result in a portion of the Ficoll-Paque to enter the bulb. Repeat this process until all the Ficoll is in the bulb and the syringe is empty.

5. Next attach the 00 ml syringe containing the buffy coat fraction and again withdraw the plunger to create a vacuum in the centrifuge apparatus, pull the plunger back until the Ficoll fluid is approaching the swabbable valve and then slowly push downward on the plunger filling the centrifuge apparatus with the buffy coat fraction. This technique results surprisingly in the blood fraction not intermingling with the Ficoll which is the required outcome of combining the two liquids. It will be observed that the disclosed technique is a simpler method than prior art to achieve the combination of the two fluids without their becoming intermingled. This technique is also faster to perform than using a pipet to layer the diluted blood sample onto the Ficoll-Paque media solution and even more importantly avoids the need for a biosafety cabinet to maintain sterility of the samples.

D. Stratification of Mixture into Density Layers by Centrifugation

Centrifuge the tube containing the blood at 400 g of acceleration for 15 minutes at 18° C. to 20° C. (centrifuge brake should be turned off).

E. Extraction of Stratified Components from Centrifuge Tube

1. Swab the valve again with alcohol and then attach a complete harvest tubing set to the pre-slit valve of the centrifuge tube using the male Luer. Attach a 10 ml syringe to the other end of the tubing set which has a pre-slit one-way valve. Draw off the upper layer containing plasma and platelets using a first syringe until the mononuclear cell layer is observed to enter the tubing. The first harvest syringe is then removed and replaced with a second harvest syringe for the purpose of harvesting the mononuclear cell band. The syringe containing the plasma may be saved for later use.

2. Transfer the mononuclear cells in the second syringe to a sterile centrifuge tube.

E. Washing the Cell Isolate

1. Estimate the volume of the transferred mononuclear cells. Add at least 3 volumes (~6 ml) of balanced salt solution to the mononuclear cells in the centrifuge tube.

2. Suspend the cells by gently drawing them in and out of a pipette.

3. Centrifuge at 400 to 500×g for 10 to 15 min at 18° C. to 20° C. Note: A centrifugation at high speed increases the mononuclear cell recovery. However, if it is important to also get rid of platelets a lower centrifugation speed is recommended (60 to 100×g).

4. Remove the supernatant.

5. Resuspend the mononuclear cells in 6 to 8 ml balanced salt solution.

6. Centrifuge at 400 to 500×g (or 60 to 100×g for removal of platelets) for 10 min at 18° C. to 20° C.

7. Remove the supernatant.

8. Resuspend the cell pellet in media appropriate for the application.

From the example above, it is apparent that the new centrifuge apparatus and method of use provides important improvements from past practices of using density media to separate mononuclear cells. Instead of doing Ficoll separation of blood which is typically done using 50 ml centrifuge tubes containing 15 ml of Ficoll, 15 ml of phosphate buffered saline and 15 ml of blood, a preferred procedure is disclosed of preparing a buffy coat fraction from a large volume of blood and only performing the density gradient step on this small fraction using the disclosed centrifuge apparatus and harvest tubing assembly. This improvement results in substantial reduction in labor and materials to obtain the desired mononuclear cell fraction in addition to the previously noted improvements of obviating the need for procedure to be performed in a biosafety cabinets to reduce the risk of microbial contamination. It is also evident that operator skill required to perform cell separation is reduced with the present invention particularly for the loading of the centrifuge tube with the density gradient media and the blood so as to avoid intermingling of the two fluids and in the extraction of the mononuclear cell band. Despite these improvements, the method of obtaining mononuclear cells using a density media is a long procedure principally due to the need to wash the isolated cells to remove the added Ficoll.

Method and Device for Isolation of Mononuclear Cells Without the Use of Density Media.

To achieve preparation of mononuclear cells from peripheral blood without the use of density media, it was learned through experimentation that the centrifuge apparatus of the present invention can achieve this unique accomplishment using the following two centrifuge step method. This achievement is of great value as it removes the need for the laborious and time consuming steps of washing away residual Ficoll with risk of unwanted cell loss and microbial contamination.

A. Selection of Centrifuge Apparatus

For the following procedure, a centrifuge apparatus is employed wherein the volume of the bulb region is 4.4 ml and the volume of the stem region is 3.5 ml.

B. Preparation of a Buffy Coat Concentrate

Fresh blood should be used to ensure high viability of isolated mononuclear cells. Prepare the sample at 18° C. to 20° C. A buffy coat preparation is prepared by centrifuging the anticoagulated whole peripheral blood in a standard centrifuge tube for a sufficient period of time to stratify to 90 ml of blood into three density layers which are platelet poor plasma, a buffy coat fraction and a packed red blood cells fraction. A suitable centrifugation speed is 2,000×g for 7 minutes. The platelet poor plasma fraction is removed and then 7 ml of buffy coat fraction collected into a 20 ml syringe. The buffy coat contains the majority of platelets and white blood cells initially present in the blood sample.

C. Loading of the Centrifuge Apparatus

1. Swab the pre-slit valve with alcohol to disinfect and then attach the 20 ml syringe containing 7 ml of buffy coat to the valve.

2. Pull the plunger on the syringe to create a negative pressure within the centrifuge device causing the bulb region to collapse and then with blood contacting the outlet of the syringe, release the plunger to fill the bulb and stem regions with the buffy coat mixture. Repeat this process until all the buffy coat fraction is in the bulb and the syringe is empty.

D. Stratification of Blood Components by Centrifugation

Centrifuge the tube containing the blood for a sufficient period to cause the stratification of the blood into a packed blood cell layer which fills the bulb and part of the stem with the white cell fraction (mononuclear cells and platelets in the upper part of the stem region of the device. A suitable centrifugation speed is 6 minutes at 3,800 rpm (centrifuge brake should be turned off).

E. Extraction of Stratified Components from Centrifuge Tube

Swab the valve again with alcohol and then attach a complete harvest tubing set to the pre-slit valve of the centrifuge tube using the male Luer. Attach a 10 ml syringe to the other end of the tubing set which has a pre-slit one-way valve. Draw off the upper layer containing mononuclear cells and platelets by pulling the plunger of the 10 ml syringe until red cells have entered the tubing and are near the end of the tubing proximate to the harvest syringe but avoiding the introduction of a stream of red blood cells which will be mixed with granulocytes into the syringe. A typical volume of harvest is between 0.7 and 2 ml of highly concentrated cells. The resulting preparation is platelet rich plasma that not only contains a high concentration of platelets but also a high concentration of monocytes and lymphocytes (mononuclear cells) and is devoid of red cells and substantially depleted of granulocytes.

The above procedure greatly simplifies the production of mononuclear cell concentrates as compared to the laborious method of using Ficoll density media and reduces the time required to obtain a useful cell concentrate preparation. This same method is also applicable to the preparation of cell concentrates from bone marrow aspirate. This technique is also very useful for the preparation of therapeutic concentrates of peripheral blood designated as platelet rich plasma.

Method for the Preparation of Platelet Concentrates from Whole Blood.

The present invention is also well suited for the preparation of platelet concentrates from whole blood with a single centrifugation step.

A. Preparation of the Blood

Fresh blood should be used to ensure high viability of isolated platelets. The use of a citrate containing anticoagulant is preferred.

B. Selection of Centrifuge Apparatus

For the following procedure, a centrifuge apparatus is employed wherein the volume of the bulb region is 4.4 ml and the volume of the stem region is 3.5 ml.

C. Loading of the Centrifuge Apparatus

1. Swab the pre-slit valve with alcohol to disinfect and then attach the 20 ml syringe containing 7 ml of blood to the valve.

2. Pull the plunger on the syringe to create a negative pressure within the centrifuge device causing the bulb region to collapse and then with blood contacting the outlet of the syringe, release the plunger to fill the bulb and stem regions with the blood. Repeat this process until all the blood is in the bulb and the syringe is empty.

D. Stratification of Blood Components by Centrifugation

Centrifuge the tube containing the blood for a sufficient period to cause the stratification of the blood into a packed blood cell layer which fills the bulb and part of the stem with the white cell fraction (mononuclear cells and platelets in the upper part of the stem region of the device. A suitable centrifugation speed is 3 minutes at 3,000 (centrifuge brake should be turned off).

E. Extraction of Stratified Components from Centrifuge Tube

Swab the valve again with alcohol and then attach a complete harvest tubing set to the pre-slit valve of the centrifuge tube using the male Luer. Attach a 10 ml syringe to the other end of the tubing set which has a pre-slit one-way valve. Draw off the upper plasma layer containing platelets by pulling the plunger of the 10 ml syringe until red cells have entered the tubing and are near the end of the tubing proximate to the harvest syringe but avoiding the introduction of a stream of red blood cells into the syringe. A typical volume of harvest is 3 ml of platelet rich plasma that has 2 to 3 times the concentration of platelets originally present in the blood. The resulting platelet rich plasma will not contain a high concentration of monocytes and lymphocytes (mononuclear cells), granulocytes or red cells.

Method for the Preparation of Platelet and Protein Concentrates from Whole Blood.

The present invention is also well suited for the preparation of plasma protein and platelet concentrates from whole blood with a single centrifugation step. The concentrator is intended to increase the concentration of plasma proteins and cells by removal of water using polyacrylate beads. The target concentration factor is 2.5-5 fold in a 15 minute process. A general summary of the device and procedure is summarized when using 11 ml of platelet rich plasma to prepare 3 ml of concentrate as an example.

A. Selection and Preparation of Centrifuge Apparatus containing Water Absorbing Beads 1. For the following procedure, a centrifuge apparatus is employed wherein the volume of the bulb region is 45 ml and the volume of the stem region is 4 ml.

2. The bulb is first loaded with approximately 330 SAP particles (1.8 mm diameter, Superabsorbent beads are a made from acrylic-acrylamide co-polymer having a dry density of 166 spheres per gram.

3. After adding the beads the centrifuge apparatus is closed to the atmosphere by the insertion of a injection site port or a pre-slit swabbable valve.

4. Next, the SAP particles is hydrated to create SAP gel beads by adding 6 mL of water using a syringe attached to the and incubated for at least 10 minutes.

5. The centrifuge apparatus is sterilized by gamma irradiation and stored until the time of preparing plasma protein concentrate with or without cell concentration.

B. Loading of the Centrifuge Apparatus

1. Swab the pre-slit valve with alcohol to disinfect and then attach the 20 ml syringe containing 7 ml of platelet rich plasma or platelet poor plasma to the valve.

2. Pull the plunger on the syringe to create a negative pressure within the centrifuge device causing the bulb region to collapse and then with plasma contacting the outlet of the syringe, release the plunger to fill the bulb and stem regions with the blood. Repeat this process until all the blood is in the bulb and the syringe is empty.

C. Removal of Water from Plasma

Incubate the mixture of SAP beads and plasma for 12 minutes during which time essentially all of the water in the plasma will be absorbed. Next inject 3 ml of plasma into the device to resuspend the cake plasma proteins on the beads.

D. Stratification of Blood Components by Centrifugation

Centrifuge the tube containing the blood for a sufficient period to cause the packing of the SAP beads in the bulb region and the supernatant of the protein and cell concentrate above the packed beads. A suitable centrifugation speed is 1 minute at 3,000 rpm (centrifuge brake should be turned off).

E. Extraction of Protein and Cell Concentrate from Centrifuge Tube

Swab the valve again with alcohol and then attach a complete harvest tubing set to the pre-slit valve of the centrifuge tube using the male Luer. Attach a 10 ml syringe to the other end of the tubing set which has a pre-slit one-way valve. Draw off the upper plasma layer containing platelets by pulling the plunger of the 10 ml syringe until as much of the protein rich fluid has entered to the harvest syringe. A typical volume of harvest is 3 ml of platelet-rich, protein-rich plasma that has 2 to 3 times the concentration of platelets and proteins originally present in the plasma initially injected into the device.

Method of Reducing the Toxicity of Cryopreserved Cell Concentrates Containing Dimethyl Sulfoxide as the Cryopreservation Agent.

The disclosed centrifuge device and harvest tubing assembly can be used in an improved method for preparing a less toxic therapeutic cell composition by removing a significant fraction of dimethyl sulfoxide (DMSO) from the mixture. Briefly, the method comprises thawing a solid frozen cell mixture containing dimethylsulfoxide until it is liquid; injecting the thawed liquid into a disclosed Type II centrifuge apparatus with sufficient capacity to hold all of the thawed liquid; centrifuging the mixture for sufficient time to create a cell pellet and substantially cell free supernatant; first removing and discarding at least a portion of the supernatant containing DMSO from the centrifuge apparatus without removing cells; and then removing essentially all cells from the centrifuge apparatus and administering the DMSO reduced cell composition to a patient.

With particular reference to FIGS. 1-4, specific details of the vial 10 are described both generically and in various embodiments for facilitating the collapsible sidewall 24 of the vial 10 of this invention. The vial 10 is a hollow elongate thin walled structure which could be formed of one or more of various different types of materials. In one embodiment, an injection moldable plastic material is utilized. The vial 10 generally includes a bulb 20 at a first end and a neck 30 extending away from the bulb 20 to a second end opposite the first end. The vial 10 is elongate in form with a greater length than cross-sectional width. The vial 10 preferably has a radially symmetrical form about an elongate central access, but this cross-sectional form varies, with the bulb 20 having a larger cross-sectional area than the neck 30. In many embodiments both the bulb 20 and neck 30 have a circular cross-section, with the bulb 20 having a greater diameter than a diameter of the neck 30.

The bulb 20 includes a floor 22 at the first end of the vial 10. Sidewalls 24 extend from the floor 22 away from the first end. The sidewall 24 and floor 22 surround an interior 25 of the bulb 20 into which a mixture is placed for separation thereof. In many embodiments a conical transition 26 is provided between the sidewalls 24 and the neck 30.

The neck 30 is preferably elongate in construction, extending from the conical transition 26 or other transition from the bulb 20 to an interface 50 at a second end of the vial 10. The neck 30 has a distal end 32 adjacent to the conical transition 26 and proximal end 34 opposite the distal end 32. A cylindrical wall 36 defines a contour of the neck 30 and is preferably formed with a circular constant cross-sectional form. A processing element 40 can be optionally provided on the neck 30 and adjacent to the interface 50 near the second and of the vial 10. As an alternative, processing elements 40 can instead be placed beyond the interface 50 and be removably attachable to the vial 10, rather than incorporated into the vial 10. The interface 50 can be a Luer lock fitting or can be some other form of fitting, such as a septum, or other interface which facilitates input and removal of fluids into and out of the interior 25 of the vial 10.

Sidewalls 24 of the bulb 20 can be configured in different ways to facilitate collapsing of the sidewalls 24. As an alternative, portions of the bulb 20 or other portions of the vial 10 adjacent to the sidewalls 24, but not necessarily including the sidewalls 24 themselves, could be configured to facilitate collapsing of the sidewalls 24. FIG. 2 depicts one embodiment where the sidewalls 24 are thinner than the conical transition 26 and other portions of the bulb 20 and neck 30 of the vial 10. By making the sidewalls 24 thinner, with thickness t rather than thickness T, the sidewalls 24 are more prone to flexibly deflecting and collapsing than other portions of the bulb 20 end of vial 10 with thickness T.

In FIG. 3 an embodiment of the vial 10 is disclosed where the sidewalls 24 (FIGS. 1 and 2) are replaced with elastic sidewalls 27. In this embodiment, the elastic sidewalls 27 might have a similar thickness T as other portions of the bulb 20 and vial 10, but be formed of a different material having different (typically greater) elasticity characteristics. For instance, the elastic sidewalls 27 might be formed of a rubber material rather than a plastic material, and having greater tendency to flex when undergoing lateral forces, such as differential pressure forces between the interior 25 and an exterior of the vial 10.

Figure 6:
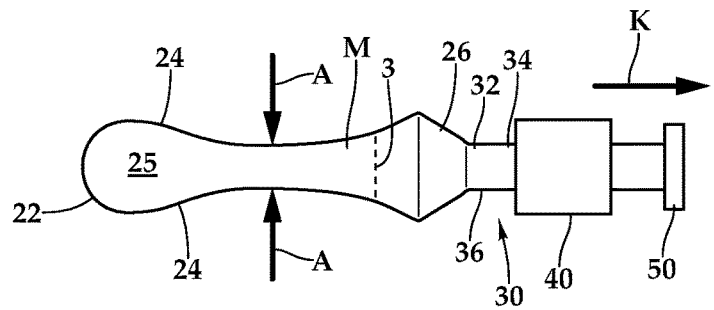

In FIG. 4 an embodiment of the vial 10 is disclosed where the sidewall 24 includes a zone of weakness (or zone of strength) 28 which extends longitudinally along a portion of the bulb 20 of the vial 10. With such a zone of weakness 28, the sidewalls 24 of the vial 10 might resist collapse otherwise, but because of the zone of weakness 28, a location exists where buckling of the sidewall 24 occurs and the sidewalls 24 can become flattened (FIGS. 6 and 11) by having the sidewall 24 flex along this zone of weakness 28. As an alternative, this zone of differential strength could be a zone of greater strength than other portions of the sidewall 24, so that the bulb 20 has its sidewalls 24 tend to buckle away from the zone of strength.

Other configurations for the sidewalls 24 could be provided to facilitate collapsing of the sidewalls 24. In one embodiment, the sidewalls 24 are no different from other portions of the vial 10, but the geometry of the vial 10 itself causes the sidewalls 24 to be the portion of the vial 10 which buckles and then flexes inward in a collapsing manner when differential pressure exists between the interior 25 and exterior of the vial 10. Such forces can be atmospheric pressure forces at least partially, or can include applying forces on an exterior of the vial 10, such as with fingers of a user, or by other force applying equipment involving motion of the sidewalls 24 lateral to an elongate central axis of the vial 10 (along arrow A of FIGS. 1-4 and 6).

With particular reference to FIGS. 5-9, details of one typical methodology for loading the vial 10 and then centrifuging a fluid mixture within the vial 10 in two separate constituent parts is disclosed, according to an illustrative embodiment. Initially, the vial 10 is typically empty (actually containing air or a gas of some sort). While a mixture to be separated, such as blood B, could be passed directly into the vial 10, most preferably the vial 10 is first caused to have its sidewalls 24 collapse (along arrow A of FIG. 6), such as by pulling air out of the interior 25 (along arrow K of FIG. 6).

Figure 11:
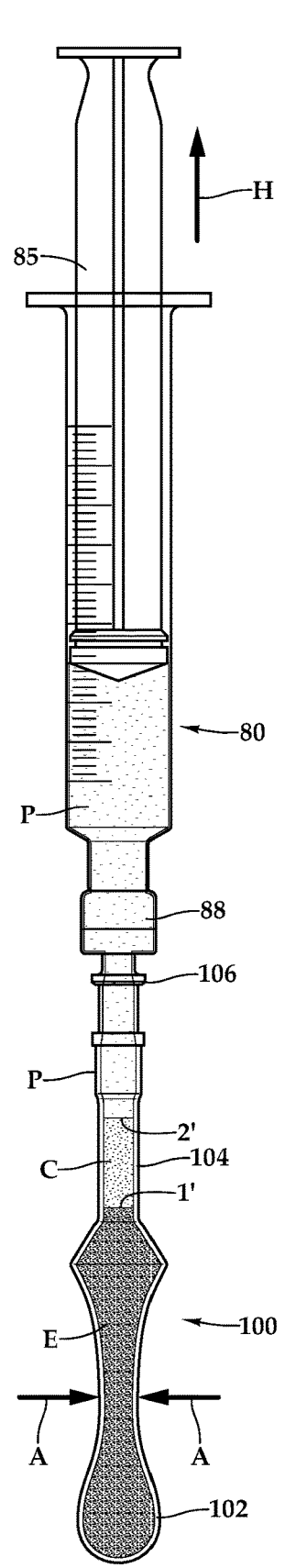

Such air evacuation could occur by attaching a syringe to the interface 50 and pulling on a plunger of the syringe (such as depicted in FIG. 11). The mixture fluid to be separated is then more easily introduced (along arrow L of FIG. 7) into the vial 10, as the bulb 20 or other portion of the vial 10 already has its sidewalls 24 collapsed, and as the fluid mixture to be separated, such as blood B, is passed into the interior 25, the sidewalls 24 can return to their original position. If a fluid mixture such as blood B is passed into the vial 10 without first collapsing the sidewalls 24, the mixture has a more difficult time passing the air already fully filling the interior 25. This can introduce bubbles into the fluid mixture and make both fluid loading and separation more difficult.

More importantly, when a medium density separation medium M is utilized to more effectively distance constituents of the mixture from each other (such as Ficoll-Paque density gradient media to separate blood B), it is necessary (or at least preferred) to first load the medium density fluid M into the interior 25 of the vial 10, and then load the mixture (such as blood B) into the vial 10, closer to the second end of the vial 10 then to the first end of the vial 10.

The best separation occurs when the medium density fluid M and the fluid mixture that is separated are not mixed together, but rather the mixture to be separated is layered carefully on top of the medium density fluid M. To keep a boundary between these two fluids precise and without mixing, initial collapsing of the sidewalls 24 before loading of the medium density fluid M, and then again collapsing the sidewalls 24 before introducing the mixture to be separated, allows for smooth and laminar flow of the two separate fluids into the interior 25 of the vial 10 without mixing, and maintaining a precise boundary therebetween. Such a boundary is depicted in broken lines as boundary three in FIGS. 6-8.

Figure 7:
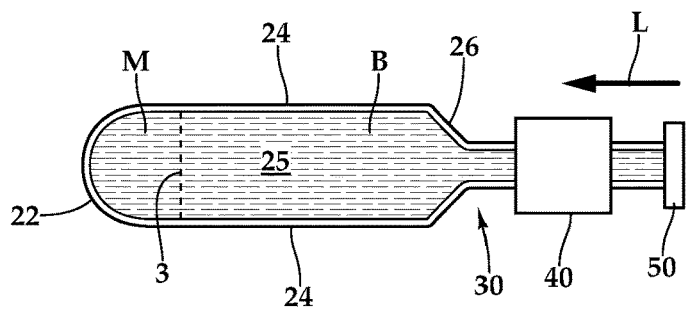

Once the vial 10 is fully loaded (as depicted in FIG. 7) it can then be placed into the centrifuge 70. Preferably this loading of the centrifuge 70 is preceded by first placing the vial 10 into a support cup 60 (FIG. 8) to support the vial 10 during centrifugation and to resist G-forces associated with centrifugation, without rupturing the vial 10, or otherwise causing undesirable deflection, especially of the bulb 20 portion of the vial 10 which might disrupt boundary layers between different constituents of the mixture as they are being separated from each other. The support cup 60 in this embodiment includes an entry 62 opposite a bottom 69. The vial 10 is passed through the entry 62 until the floor 22 of the bulb 20 is adjacent to the bottom 69. The shape of the bottom 69 matches the shape of the floor 22, as well as a size of the floor 22 in this embodiment.

The chamber 64 within the support cup 60 holds the vial 10 therein. A wall 68 extends from the bottom 69 up to a rim 66 surrounding the entry 62. An optional support cap 65 can fit snugly adjacent to the rim 66 and inboard of the wall 68 to support portions of the vial 10 including the neck 30 and other portions of the vial 10 adjacent to the second end of the vial 10, if desired.

Figure 9:
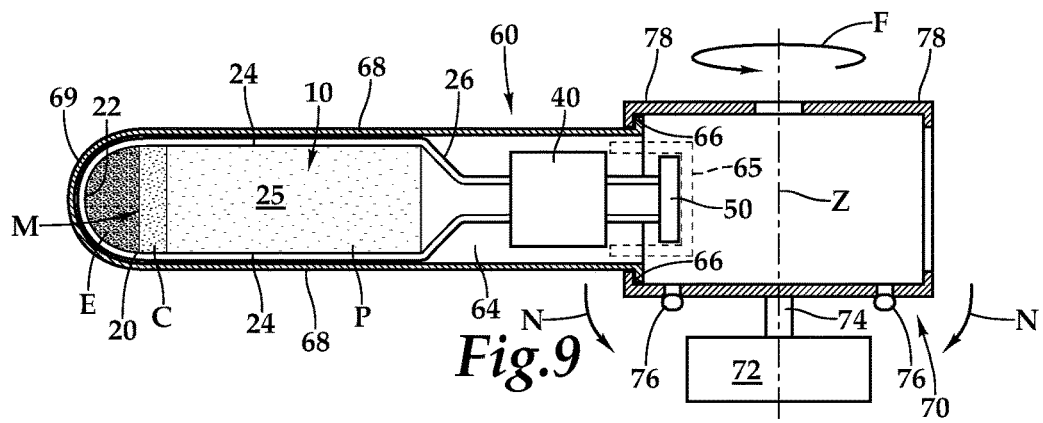

Different centrifuges can be loaded in different ways. FIG. 9 depicts a centrifuge 70 which has cupholders 78 which are sized to hold a rim 66 of a support cup 60 therein. These cupholders 78 pivot about hinges 76 (along arrow N of FIG. 9) which is also attached to an output shaft 74 coupled to a motor 72. When centrifuge 70 is at rest, the cupholders 78 hold the vial 10 within the support cup 60 in a vertical orientation with the first end of the vial 10 below the second end of the vial 10. As the motor 72 causes the output shaft 74 and associated cupholder 78 to rotate (about arrow F of the rotational axis Z), the support cup 60 and associated cupholders 78 pivot about the hinges 76 (along arrow N) until they extend horizontally away from the rotational axis Z. After a suitable period of time, the original fluid mixture has been separated into separate constituent fractions. When the initial mixture is blood B, typical fractions include erythrocytes E (also referred to as red blood cells or hematocrit) adjacent to the floor 22 of the bulb 20 or other first and portion of the vial 10. If a medium density fluid M was introduced into the interior 25, it would typically be adjacent to a side of the erythrocytes E opposite the floor 22. The next layer is typically a buffy coat C layer which, depending on the original mixture provided, is a concentration of white blood cells, leukocytes, platelets and/or stem cells.

This buffy coat C or other intermediate fraction is especially optimized for harvesting and extraction from the vial 10 with the particular vial 10 system and method of this invention. On the side of the buffy coat C opposite the erythrocytes E, a plasma layer is provided, which can be platelet rich plasma in some embodiments. While the separate constituents are typically relatively clearly and precisely stratified after centrifugation, it can be difficult to separate different layers with a high yield, and without introducing appreciable contamination. The vial, system and method of this invention is particularly optimized to simplify and improve such procedures to achieve high yield pure constituent samples simply and effectively.

Figure 10:
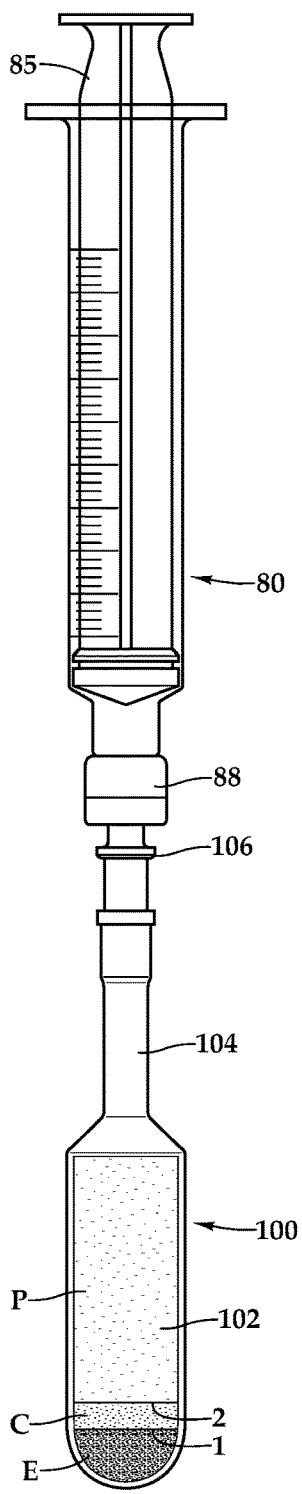
FIGS. 10 and 11 are side elevation views of alternative embodiment vials coupled to a syringe and illustrating how vial sidewall collapse can facilitate removal of different constituents of a separated fluid mixture, in an especially laminar fashion and with high visibility of small constituent fractions being facilitated by vial sidewall collapse.

One method for extraction of constituent fractions from the vial 10, such as using a simple vial 100 are depicted in FIGS. 10 and 11. This vial 100 is generally similar to the vial 10 of FIGS. 1-9, but is depicted without the processing element 40 and has a slightly longer neck 104 extending away from a bulb 102 to a female Luer lock tip 106 defining one form of interface for the vial 100. In FIG. 10, a syringe 80 has been attached through a port 88 on the syringe 80 to the female Luer lock tip 106. A plunger 85 of the syringe 80 is fully collapsed into a barrel of the syringe 80 and is ready to be pulled (along arrow H of FIG. 11) to draw at least a partial vacuum on an interior of the simple vial 100. Blood B (FIG. 8) has been separated into erythrocytes E, separated by boundary 1 from a buffy coat layer C. The buffy coat layer C is separated by a boundary 2 from plasma P, all contained within the bulb 102.

When the plunger 85 is retracted (along arrow H of FIG. 11) flexible sidewalls of the vial 100 are compressed toward each other (along arrow A of FIG. 11) collapsing a cross-sectional area of at least portions of the bulb 102 and causing a volume of the bulb 102 to be reduced. In this depiction, the volume of the bulb 102 is decreased so much that the erythrocytes E now fill the highly reduced volume of the bulb 102. This moves the buffy coat fraction C into the neck 104, with some portion of the plasma also in the neck 104, and passing through and into the syringe 80.

With the bulb 102 and neck 104 formed of transparent (or at least partially transparent) material, and with the different layers each being visually distinct from each other, a user can pull back on the plunger 85 of the syringe 80 (along arrow H) and watch the neck 104, to see the transition lines move, such as to the new locations depicted in FIG. 11 by transition boundaries 1' and 2'. Because these boundaries 1' and 2' are further apart in the neck 104 than they were within the bulb 102 (FIG. 10, and depicted by boundary lines 1 and 2), a user pulling on the plunger 85 of the syringe 80 can more precisely monitor the position of the buffy coat C within the neck 104. In this way, when the syringe 80 has removed all of the plasma from the simple vial 100, the syringe 80 can be disconnected from the vial 100 and a separate syringe utilized for simple and precise further extraction of the buffy coat C fraction. As another alternative, the buffy coat C fraction could be drawn into the tip of the syringe 80 and then discharged from the syringe 80 into a collection container.

As further alternatives, a stopcock (FIG. 24) could be interposed between the syringe 80 and the vial 100 and the stopcock pathways adjusted after the plasma P has been removed and so that the buffy coat C can be collected in a separate syringe on a separate port of the stopcock. As another alternative, a valve (such as a swabbable tip) can be provided at the second end of the vial 100 so that when a syringe 80 is removed, the bulb 102 remains collapsed. Then a new syringe can be attached for the extraction, and without allowing return of the collapsed sidewalls of the bulb 102 of the vial 100 until the buffy coat C (or other target component) has been extracted into the new syringe.

Furthermore, experimentation has shown that boundary lines 1 and 2 remain precise and unmixed as these boundary lines move within an interior of the vial 100, when the vial has a flexible side wall which is collapsed inwardly during extraction. No air bubbles or other gases are introduced into the vial 100 to allow for extraction by pushing contents of the vial out of the vial. Rather, as the collapsible sidewalls of the vial collapse, the separated constituents merely move slowly upwardly in a manner which resists mixing between different constituents. With the boundaries remaining precisely in place, a higher yield of desired fractions can be achieved and higher purity of desired fractions can be achieved. Furthermore, less skill and greater speed can be involved and still produce high-quality results.

Figure 12:
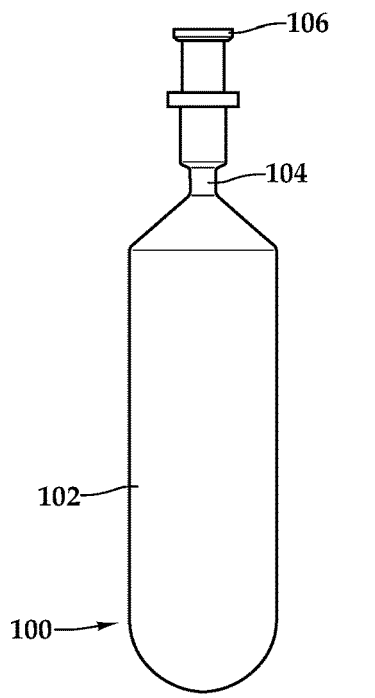
FIG. 12 is a side elevation view of a centrifugation vial such as that shown in FIGS. 10 and 11, but shown separate from the syringe to illustrate details of the interface, and including a female Luer lock tip as one interface for vials according to this invention.

With particular reference to FIGS. 12-24 various different modifications to centrifugation vials featuring collapsible sidewalls are disclosed, with these various vials having slightly different geometries and different interfaces and different processing elements to optimize the vials for use in various different separation methodologies and to achieve various different results according to various different aspects of this invention. In FIG. 12 the same simple vial 100 as that depicted in FIGS. 10 and 11 is depicted, but with a slightly shorter and smaller diameter neck 104. In some embodiments the neck 104 has about ⅓ the cross-sectional area as the cross-sectional area of the bulb 102, so that fractions within the bulb are approximately three times longer in an elongate direction when they have transitioned into the neck 104 from the bulb 102. However, the cross-sectional area ratios between the neck 104 and bulb 102 can vary, such as with that depicted in FIG. 12 being more correlative to a neck having a cross-sectional area approximately ¹⁄₁₀ of a cross-sectional area of the bulb 102, so that fractions within the neck 104 (or within a syringe having a similarly small cross-sectional diameter as that provided in the neck 104) are approximately ten times longer than a length of the same constituent layer within the bulb 102. As an example, a constituent fraction layer that is only 1 mm tall within the bulb 102 would be 10 mm tall within the neck 104.

Figure 13:
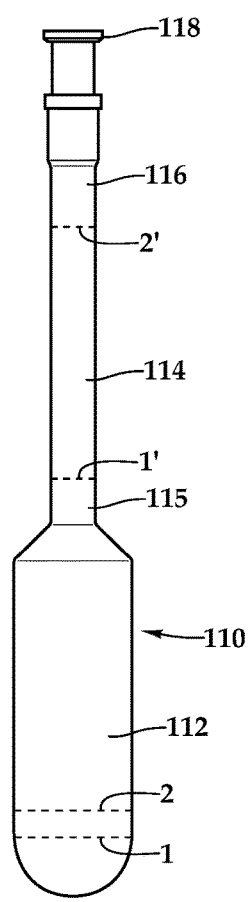
FIG. 13 is a side elevation view of an alternative embodiment of that which is shown in FIG. 12 featuring a longer neck, and with broken lines illustrating various different transition lines between layers of constituents after centrifugation within such a vial, and illustrating how a long and slender neck can provide for a thin layer to be visually enlarged for most effective handling thereof.

With particular reference to FIG. 13, a long neck vial 110 is depicted including a bulb 112 and a long neck 114 which is longer than the bulb 112. The long neck 114 extends between a distal end 115 to a proximal end 116. Transition lines between constituents separated from a mixture are depicted by lines 1 and 2 with in the vial 110. During extraction and when the bulb 112 has sidewalls thereof collapsed to decrease volume of the bulb 112, these boundary lines 1, 2 transition into boundary lines 1' and 2' within the neck, and are significantly further spaced from each other and easily visualized as they extend toward the female Luer tip 118 for extraction from the vial 110. Precise removal of the desired intermediate competent, such as the buffy coat C (FIG. 10) can thus more easily be achieved.

Figure 14:
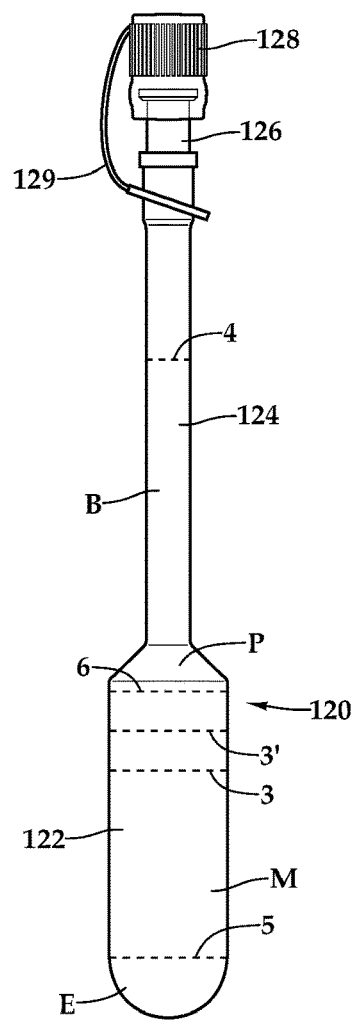
FIG. 14 is a side elevation view of a further alternative embodiment vented vial, with transition lines shown in broken lines thereon to illustrate how two transition lines between constituent layers can be manipulated with a vial having a bulb with a collapsible sidewall, especially when a medium density fluid is also introduced into the vial during centrifugation.

In FIG. 14 a similar long neck vial 110 is modified as a vented cap vial 120 with a bulb 122 and neck 124 similar to the long neck vial 110, but with the neck 124 terminating at a vented cap 128 including a lanyard 129 to hold the vent cap 128 to the neck 124 when removed from the female Luer tip 126. Superimposed upon the vented cap vial 120 in FIG. 14 are boundary lines 5 between erythrocytes E and a medium density fluid M. Further boundary line 3 is shown above the medium density fluid M. This boundary line 3 is provided between blood B and the medium density fluid M before centrifugation. When centrifugation occurs, the erythrocytes E are transported through the medium density fluid M down to the first end of the vial 120. This moves the medium density fluid M upward slightly within the bulb 122 of the vial 120, and in turn causes the boundary 3 to move up to the new location after centrifugation depicted by boundary 3'.

Boundary 6 depicts an upper edge of the buffy coat C or other intermediate density fraction of the blood B after centrifugation. Above that boundary 6 the plasma P of the blood B is provided and extends up to the upper fluid boundary 4 within the neck 124. Utilization of the vented cap 128 on the vial 120 allows the vial 120 to be optimized for cell culture and cell conditioning activities. In the category of cell culture activities, this can include IRAP production, cell washing (DMSO removal from stem cells or Ficoll removal), or cell conditioning, such as with hypoxia activators.

Figure 15:
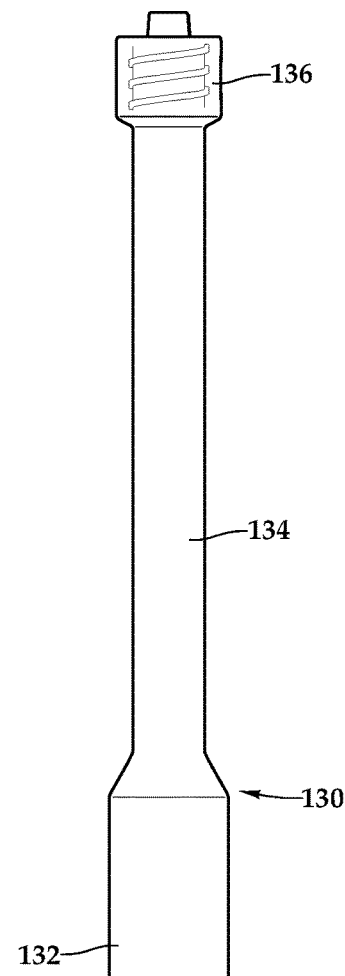
FIG. 15 is a side elevation view of a further alternative embodiment vial having a male luer lock tip and long neck featured thereon.

In FIG. 15 another long neck vial 130 is depicted which includes a bulb 132 and neck 134 with the neck 134 significantly longer than the bulb 132 and terminating at a male Luer lock tip 136. The neck 134 in this embodiment is closer to the diameter of the bulb 132. The neck 134 is preferably stiffer than the bulb 130 provide a neck 134 which does not undergo collapse when experiencing differential pressure between an interior and exterior. However, the neck 134 could be configured to also collapse at least somewhat. The male Luer tip 136 allows for attachment to different ports within manifolds and ports of stopcocks and other fluid handling equipment.

In FIG. 16 a septum interface vial 140 is depicted with a bulb 142 and neck 144 which are similar to those of the vial 130 (FIG. 15). However, the interface is provided as a septum 146. A needle 149, such as that associated with a syringe 148 can pass through the septum 146 (along arrow I of FIG. 16) to allow for input and/or output of fluids relative to an interior of the bulb 142 for sterile environment maintenance, especially if an interior of the vial 140 is sterilized during manufacture. Various methodologies associated with other vials and depicted above can be performed through such a septum 146 utilizing a syringe 148 and needle 149, rather than requiring fluid handling tubing which can be preferential in many embodiments.

In FIG. 17 a particle filter vial 150 is provided with a bulb 152 and neck 154 which are generally similar in geometry to the simple vial 100 depicted in FIG. 12. However, processing elements such as a particle filter housing 156 are provided at a second end of the vial 150, along with a swabbable tip 158 which typically includes a one-way valve therein or a valve which closes off an interior of the particle filter vial 150, except when a syringe or other fitting is inserted into the swabbable tip 158. In this particular embodiment depicted in FIG. 17 the bulb 152 contains SAP water extraction beads S. Some separation procedures benefit from having such water extraction beads S, which are typically some form of polymer gel, contained within the bulb 150. These beads S can absorb water from at least one fraction, such as after or during centrifugation, and to allow for greater concentration of other constituents within a mixture.

As another option, such reduction of water content with water absorbent beads or other water absorbent substances can occur without being related directly (or indirectly) to any centrifugation step. For instance and as an example, an aqueous mixture derived from a body fluid can contain cells such as platelets, leukocytes, stem cells or macromolecules such as nucleic acids and proteins having a molecular weight of greater than 30,000 kilodaltons which cannot enter into the water absorbing beads due to their size can be placed into the vial 150 containing the SAP water extraction beads S, and the aqueous mixture will, over time (e.g. five minutes), have at least a portion of water (or some water containing fraction of the mixture) absorbed by the SAP water extraction beads S or other water absorbent substance within the vial. This water absorption step results in an increased concentration of cells and/or an increased concentration of macromolecules such as nucleic acid or proteins at an increased concentration than originally present in the starting aqueous solution. A remaining second complement of the mixture which is not absorbed by the water absorbent substance remains free within the vial at a higher concentration. A syringe or other fluid extraction device can be coupled to the swabbable tip 158 or other inlet/outlet of the vial 150, and the second component can be extracted from the vial 150.

A first component which was absorbed by the water absorbent substance remains within the vial 150. To keep this first component within the vial, either the beads S or other water absorbing substance can be sufficiently large that it cannot pass through the inlet, or a particle filter housing 156 can be provided which keeps the beads S within the vial 150. In one embodiment, the beads S swell as they absorb water or a water containing first component of the mixture. The filter housing 156 could in one embodiment be sized so that the beads S or other water absorbing substance is small enough before absorbing the water or water containing first component to fit through the filter element in the filter housing 156, but the filter element is small enough to prevent exit of the beads S or other water absorbing substance after swelling by absorbing the first component. In such an arrangement, the beads S can be readily placed into the vial 150, but will become entrapped within the vial 150 during extraction. By providing the vial 150 with a collapsible sidewall, an interior of the vial 150 can remain isolated from the surrounding atmosphere and still have fluids readily removed therefrom, in that no air, gases or other liquids need to be introduced into the interior of the vial 150 to allow for removal of contents from within an interior of the vial 150.

This method is particularly useful for preparing concentrates of biological fluids for the preparation of novel therapeutic aqueous compositions comprised of cell concentrates suspended in a protein concentrate. A particularly useful and novel composition is the removal of water from a preparation of platelet rich plasma so as to prepare a platelet concentrates suspended in plasma that has increased concentrations of fibrinogen and alpha-2-macroglobulin. It is possible to achieve concurrent increases in the concentration of platelets, fibrinogen and alpha-2-macroglobulin up to 4 times the original concentration using the disclosed method. The disclosed method is also particularly useful for preparing concentrates of biological fluids for the preparation of samples for diagnostic purposes based on either detection of nucleic acids of infectious agents or presence of pathogenic organisms to improve the sensitivity of the test method by concentrating the detected analyte using the water absorption process prior to conducting the diagnostic test. This technique can be used to improve the sensitivity of diagnostic tests by the concentrating of viruses, bacteria, fungi, protozoa, worms and tumor cells or molecules derived from the same in aqueous samples.

In FIG. 18 a sterile filter vial 160 is depicted with a bulb 162 and neck 164 which generally match geometry of the simple vial 100 (FIG. 12). However, the neck 164 has a proximal upper end which has a sterile filter 166 attached thereto, which also typically has a vented cap 168 attached to the sterile filter 166, and held by a lanyard 169 to the neck 164, so that the vented cap 168 can be removed and replaced without becoming separated from the vial 160. In FIG. 19 the simple vial 100 has a bulb 102 and neck 104 along with a female Luer lock tip 106 which is attached to extension tubing 108, optionally transparent for fraction visualization, leading to a swabbable tip 109 which can be placed distant away from the simple vial 100 for further effective fluid handling in many circumstances.

Figure 20:
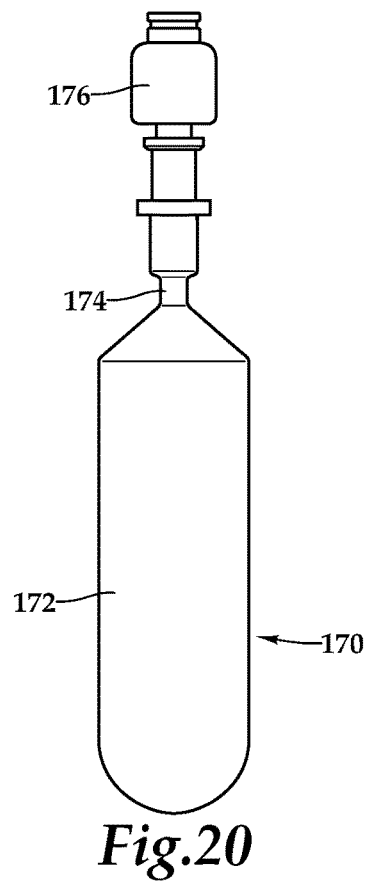
FIG. 20 is a side elevation view of a closed system vial for use in separation procedures without requiring a biosafety cabinet, but rather having a swabbable and sterilizeable tip thereon.

In FIG. 20 a closed system vial 170 is depicted with a bulb 172 and neck 174 generally matching the simple vial 100 (FIG. 12), but with a swabbable tip 176 located at an interface thereof. Such a swabbable valve can readily maintain sterility, and is useful for cell separation, self storage/transport, cryogenic storage and sell washing, among other uses. With the swabbable valve 186, a sterile environment can be readily maintained within the vial 170, so that various different fluid transfer activities can occur with other sterile containers and steps of various methods can be performed without special hoods or other sterile environments and maintain a desired sterile environment for fluids being handled therein.

Figure 21:
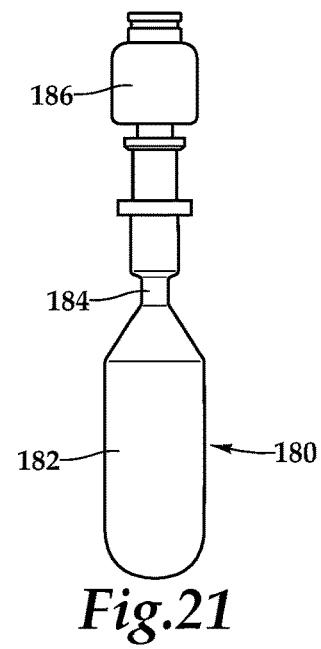
FIG. 21 is a side elevation view of a cryo-vial for use both in separation and later utilization in cryo-procedures, and generally featuring a smaller size than other embodiments.

In FIG. 21 a cryo vial 180 is depicted which is similar to the closed system vial 170 except that it is smaller with a smaller bulb 182, and a neck 184 which can be similar to other necks or smaller than such other necks. A swabbable valve 186 can also be supplied. With smaller contents of the bulb 182, the bulb 182 is more conducive to rapid freezing, and with the smaller footprint can be maintained in a cryo-environment without taking up as much space, and is more desirable for small samples which do not require the larger volumes of other vials.

Figure 22:
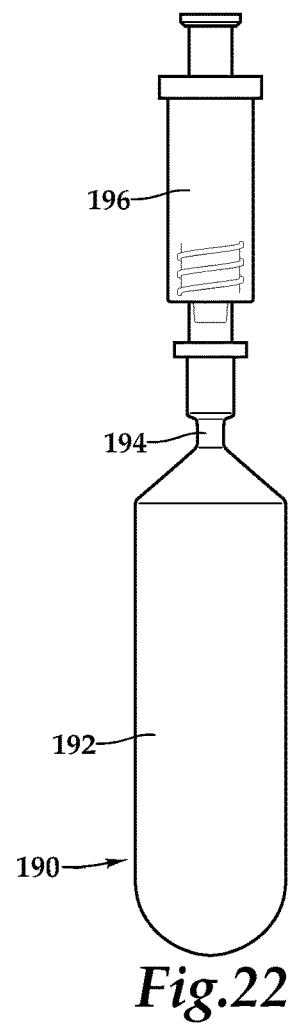
FIG. 22 is a side elevation view of a valve vial including a valve as a processing element on the vial, such as a one-way valve, to facilitate operation within processes where limiting flow to a single direction is desired.

FIG. 22 depicts a valve vial 190 with a bulb 192 and neck 194 similar to other embodiments, but with an interface in the form of a non-swabbable valve 196. This non-swabbable valve 196 facilitates connection to complementally formed structures.

Figure 23:
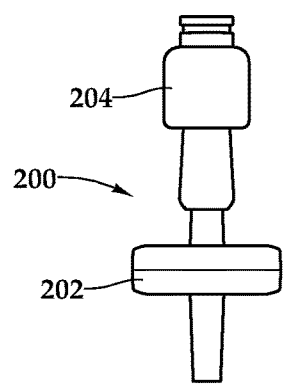
FIG. 23 is a side elevation view of an extractor element attachable to one of the vials of this invention to facilitate optimal extraction from the vial after centrifugation.
Figure 24:
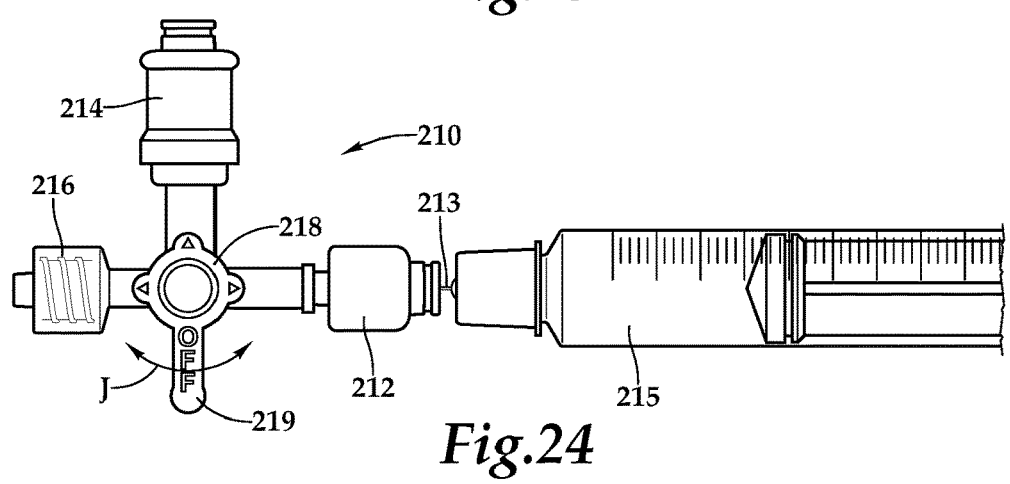
FIG. 24 is a side elevation view of a stopcock extractor similar to that which is shown in FIG. 23, but including a stopcock with different ports thereon, such as with a port coupled to a syringe or to other fluid handling structures, and with a vial attachable to such a stopcock extractor, such as to facilitate a first constituent such as plasma being removed into a first vessel and a second constituent such as a stem cell rich layer can be extracted into a second vessel separate from the first vessel.

In FIGS. 23 and 24 an extractor 200 and stopcock extractor 210 are depicted. Such extractors 200, 210 can be coupled to various different vials such as those depicted above, such as by press fitting of a tip thereof (bottom of FIG. 23) into an interface of a vial. Some form of selective pathway 202 can be provided on the extractor 200 and a swabbable tip 204, if desired, which interface with a syringe or can include a septum and interface with a needle 213 of a syringe 215. In the case of the stopcock extractor 210, a septum interface 212 separate from a syringe interface 214 and a vial interface 216 can be coupled to different ports of a valve body 218 to be selected for fluid communication between various different ports by selector 219 (through rotation along arrow J).

If the vial interface 216 is coupled to a vial such as those depicted above, after separation has occurred, a syringe interface 214 can be utilized to pull off plasma P (FIG. 11), and then a syringe 215 with needle 214 can interact with the septum interface 212 to draw off the buffy coat C or other harvest fraction. Such a harvest fraction could be then immediately utilized by discharge from the needle 213 of the syringe 215, or transferred, such as to a storage container for later processing and/or use.

Figure 25:
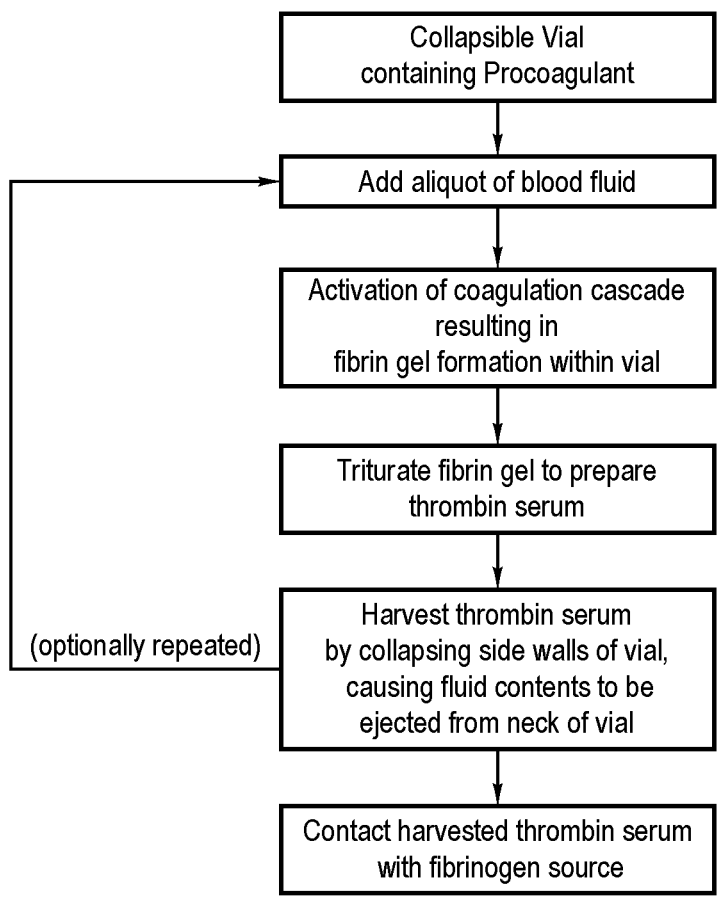
FIG. 25 is a flow chart illustrating steps in a thrombin serum preparation process which can be used with a collapsible sidewall vial such as those disclosed herein, and without necessarily involving centrifugation.

With particular reference to FIG. 25, a method of thrombin serum preparation has representative steps thereof illustrated in the form of a flow chart. This thrombin serum preparation process can be effectively performed utilizing a vial having a collapsible sidewall, such as many of the vials disclosed herein. In performing this method, a procoagulant agent and a triturating agent are contained within such a vial, along with a source of prothrombin and fibrinogen to form a mixture comprising fibrin gel. The mixture is then triturated to prepare thrombin serum. At least a portion of the thrombin serum can then be removed from the vial while allowing the collapsible sidewall of the vial to collapse to reduce vial volume. The fibrin gel is formed within the vial by adding an aliquot of blood fluid into the vial which contacts the procoagulant and initiates activation of a coagulation cascade resulting in the fibrin gel formation within the vial.

Suitable procoagulant agents and triturating agents as well as suitable sources of prothrombin and fibrinogen are disclosed in U.S. Pat. No. 9,480,730, the entire contents of which are incorporated herein by reference. The procoagulant agent is in various embodiments selected from the list comprising but not limited to glass, glass beads, glass fibers, ceramic, ellagic acid, and diatomaceous earth or the like that is associated with a functional prothrombinase enzyme complex and defined as activated procoagulant. One procoagulant agent is borosilicate glass beads having a diameter of between 50 microns and 2 mm, such that they are easily retained within the reaction chamber whilst allowing blood cells to pass (approximately 6-10 micron diameter) by means readily known to those skilled in the art such as filter screen, depth filters and the like. It is advantageous to provide a large surface area for the procoagulant agent to lie on the bottom of the reaction chamber.

It is advantageous to include in the reaction chamber other detached objects having a larger diameter and greater mass (than the procoagulant agent) to be used for triturating formed fibrin gels by physical agitation such as manually shaking the apparatus. Exemplary suitable detached objects are 6 to 8 mm beads prepared from medically acceptable materials for blood contact, such as glass, polystyrene, polycarbonate and polyethylene, although it should be readily understood that other triturating agents may be utilized. Preferably, all portions of the apparatus are biocompatible with human use and may withstand sterilization by one or more known sterilizing methods including gamma irradiation, e-beam or less preferably ethylene oxide gas.

The vial can include a filter element so that during harvest of thrombin serum the triturating agent and/or procoagulant agent remain within the vial. The process can be repeated by repeating the step of adding the aliquot of blood fluid after harvesting the thrombin serum one or more times. Finally, the harvested thrombin serum is contacted with a fibrinogen source. The vial with collapsible sidewall provides for convenient loading and especially ejection, in a bio safe environment if the vial includes a swabbable tip or other valve, such as at the inlet.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When embodiments are referred to as "exemplary" or "preferred" this term is meant to indicate one example of the invention, and does not exclude other possible embodiments. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A method for separation of components of a fluid mixture, the method including the steps of:

loading a vial with the fluid mixture, the vial having a first end opposite a second end, and with a collapsible sidewall extending at least partially between the first end and the second end, and with an inlet spaced from the first end;

rotating the vial in a centrifuge about a rotational axis, with the first end further from the rotational axis than the second end, until the fluid mixture is at least partially separated into at least two components, including a first component and a second component, the first component closer to the first end of the vial than the second component;

ejecting at least a portion of the second component of the fluid mixture from the vial through the inlet by collapsing the sidewall of the vial to reduce vial volume; and wherein said loading step includes the vial having a bulb adjacent to the first end, and with a neck extending from the bulb toward the second end, said bulb having a larger cross-sectional area perpendicular to a long axis, extending between the first end and the second end, than a cross-sectional area of the neck.

2. A method for separation of components of a fluid mixture, the method including the steps of:

loading a vial with the fluid mixture, the vial having a first end opposite a second end, and with a collapsible sidewall extending at least partially between the first end and the second end, and with an inlet spaced from the first end;

rotating the vial in a centrifuge about a rotational axis, with the first end further from the rotational axis than the second end, until the fluid mixture is at least partially separated into at least two components, including a first component and a second component, the first component closer to the first end of the vial than the second component;

ejecting at least a portion of the second component of the fluid mixture from the vial through the inlet by collapsing the sidewall of the vial to reduce vial volume; and wherein said loading step is preceded by collapsing the vial to have a lesser volume, with said vial increasing in volume as said loading step occurs.

3. A method for separation of components of a fluid mixture, the method including the steps of:

loading a vial with the fluid mixture, the vial having a first end opposite a second end, and with a collapsible sidewall extending at least partially between the first end and the second end, and with an inlet spaced from the first end;

rotating the vial in a centrifuge about a rotational axis, with the first end further from the rotational axis than the second end, until the fluid mixture is at least partially separated into at least two components, including a first component and a second component, the first component closer to the first end of the vial than the second component;

ejecting at least a portion of the second component of the fluid mixture from the vial through the inlet by collapsing the sidewall of the vial to reduce vial volume; and wherein said loading step includes repeatedly pressing at elevated pressure the fluid mixture into the vial from a syringe through the inlet, followed by withdrawing gas from the vial at reduced pressure into the syringe, with the syringe located above the vial.

4. A method for separation of components of a fluid mixture, the method including the steps of:

loading a vial with the fluid mixture, the vial having a first end opposite a second end, and with a collapsible sidewall extending at least partially between the first end and the second end, and with an inlet spaced from the first end;

rotating the vial in a centrifuge about a rotational axis, with the first end further from the rotational axis than the second end, until the fluid mixture is at least partially separated into at least two components, including a first component and a second component, the first component closer to the first end of the vial than the second component;

ejecting at least a portion of the second component of the fluid mixture from the vial through the inlet by collapsing the sidewall of the vial to reduce vial volume; and wherein said ejecting step includes applying a differential pressure between an exterior of the sidewall and an interior of the vial, with the pressure within the interior of the vial being lower than the pressure at the exterior of the sidewall.

5. The method of claim 1 wherein said rotating step is preceded by a step of placing the vial within a support cup, the support cup having an interior shaped and sized to contact the vial and provide structural support to the vial at least at the first end of the vial.

6. The method of claim 1 wherein the fluid mixture includes a biological fluid, and wherein said first component includes red blood cells at a greater concentration than a concentration of red blood cells in the biological fluid.

7. The method of claim 6 wherein said second component includes plasma, and wherein said rotating step includes rotating the fluid mixture until at least three components are stratified by their relative density from each other, including a third component located between the first component and the second component that is enriched in concentration for platelets and white blood cells relative to the biological fluid; and further removing the third component from the vial after said step of ejecting at least a portion of the second component of the fluid mixture from the vial.

8. The method of claim 7 wherein said loading step is preceded by a step of loading the vial with a medium density separation fluid, having a density between a density of the first component and a density of the second component, and with the medium density separation fluid having a density distinct from a density of the third component.

9. A method for separation of components of a fluid mixture, the method including the steps of:

loading a vial with the fluid mixture, the vial having a first end opposite a second end, and with a collapsible sidewall extending at least partially between the first end and the second end, and with an inlet spaced from the first end;

rotating the vial in a centrifuge about a rotational axis, with the first end further from the rotational axis than the second end, until the fluid mixture is at least partially separated into at least two components, including a first component and a second component, the first component closer to the first end of the vial than the second component;

ejecting at least a portion of the second component of the fluid mixture from the vial through the inlet by collapsing the sidewall of the vial to reduce vial volume; and wherein said collapsing of the sidewall of the vial is caused at least partially by applying a vacuum to an interior of the vial through the inlet.

10. The method of claim 1 wherein said collapsing of the sidewall of the vial is caused at least partially by applying force inwardly upon the collapsible sidewall of the vial.

* * * * *